(12) United States Patent
Danitz et al.

(10) Patent No.: US 11,931,570 B2
(45) Date of Patent: Mar. 19, 2024

(54) TREATING TISSUE PULSED ENERGY USING HIGH-VOLTAGE CATHETERS

(71) Applicant: Pulse Biosciences, Inc., Hayward, CA (US)

(72) Inventors: David J. Danitz, San Jose, CA (US); Kevin L. Moss, Lathrop, CA (US); Wesley C. Joe, Mountain View, CA (US); Christopher J. Foster, San Francisco, CA (US); Gary L. Boseck, San Carlos, CA (US); Xitlalic Y. Soto-Sida, Santa Clara, CA (US); Robert Maston, Santa Cruz, CA (US); John P. Lunsford, Los Altos, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 0 days.

(21) Appl. No.: 18/149,665

(22) Filed: Jan. 3, 2023

(65) Prior Publication Data

US 2023/0149710 A1    May 18, 2023

Related U.S. Application Data

(62) Division of application No. 16/789,350, filed on Feb. 12, 2020, now Pat. No. 11,571,569.

(Continued)

(51) Int. Cl.
*A61N 1/04* (2006.01)
*A61B 34/35* (2016.01)
(Continued)

(52) U.S. Cl.
CPC .......... *A61N 1/36017* (2013.01); *A61B 34/35* (2016.02); *A61N 1/0476* (2013.01);
(Continued)

(58) Field of Classification Search
CPC .. A61N 1/36017; A61N 1/0476; A61N 1/048; A61N 1/06; A61N 1/08;
(Continued)

(56) References Cited

U.S. PATENT DOCUMENTS 5,074,802 A   12/1991  Gratziani et al.
5,417,208 A    5/1995  Winkler
(Continued)

FOREIGN PATENT DOCUMENTS

CA    2838411 A1    1/2005
EP    1201198 A1    5/2002
(Continued)

OTHER PUBLICATIONS

Anand et al., "Nano-Pulse Electro-Signaling treatment of murine tumors significantly reduces the percentage of regulatory T cells in the treated tumor," Journal for Immunotherapy of Cancer: 31 St Annual Meeting and Associated Programs of the Society for Immunotherapy of Cancer (SITC 2016), Part Two, National Harbor, MD, USA; p. 214; Nov. 16, 2018.
(Continued)

*Primary Examiner* — Carl H Layno
*Assistant Examiner* — Anh-Khoa N Dinh
(74) *Attorney, Agent, or Firm* — Shay Glenn LLP

(57) ABSTRACT

Flexible catheters adapted to be inserted into a body to deliver high-voltage, fast (e.g., microsecond, sub-microsecond, nanosecond, picosecond, etc.) electrical energy to target tissue may include a plurality of conductive layers, that may be coaxial. These catheters and method of using them to treat tissue are configured to reduce or avoid arcing.

23 Claims, 19 Drawing Sheets

Related U.S. Application Data

(60) Provisional application No. 62/806,750, filed on Feb. 15, 2019.

(51) Int. Cl.
*A61N 1/06* (2006.01)
*A61N 1/08* (2006.01)
*A61N 1/36* (2006.01)
*A61N 1/375* (2006.01)
*A61N 1/378* (2006.01)
*H03K 3/02* (2006.01)
A61B 34/30 (2016.01)

(52) U.S. Cl.
CPC ............ *A61N 1/048* (2013.01); *A61N 1/06* (2013.01); *A61N 1/08* (2013.01); *A61N 1/3603* (2017.08); *A61N 1/375* (2013.01); *A61N 1/378* (2013.01); *H03K 3/02* (2013.01); A61B 2034/301 (2016.02); A61N 2001/083 (2013.01)

(58) Field of Classification Search
CPC ...... A61N 1/3603; A61N 1/375; A61N 1/378; A61N 2001/083; A61N 1/0565; A61N 1/3625; A61N 1/365; A61N 1/205; A61N 1/37; A61B 34/35; A61B 2034/301; A61B 18/1477; A61B 2018/00577; A61B 2018/00982; A61B 2018/126; A61B 18/1206; A61B 18/1492; A61B 2018/1467; A61B 2018/00267; A61B 2018/00351; A61B 2018/00541; A61B 2018/124; A61B 2018/1475; H03K 3/02; A61F 2/2427; A61F 2/2442; A61F 2/2454; A61F 2/2457; A61F 2/2466; A61F 2220/0008; A61F 2220/0016; A61F 2250/0097; A61M 2039/0646; A61M 39/06; A61M 5/14; A61M 2205/054; A61M 25/0051; A61M 25/0053; A61M 25/0127; A61M 2025/0161; A61M 2025/09166; A61M 2205/0216; A61M 25/0009; A61M 25/005; A61M 25/0108; A61M 25/0133; A61M 25/0147; A61M 25/09041; A61M 2205/3306; A61M 2205/332; A61M 2205/3331; A61M 2205/3592; A61M 2205/583; A61M 25/002; A61M 25/0097; A61M 25/0113; A61M 25/09; A61M 25/10

See application file for complete search history.

(56) References Cited

U.S. PATENT DOCUMENTS

| | | | |
|---|---|---|---|
| 5,568,035 A | 10/1996 | Kato et al. |
| 5,569,220 A | 10/1996 | Webster, Jr. |
| 5,635,776 A | 6/1997 | Imi |
| 5,774,348 A | 6/1998 | Druce et al. |
| 5,827,272 A | 10/1998 | Breining et al. |
| 5,902,272 A | 5/1999 | Eggers et al. |
| 5,907,484 A | 5/1999 | Kowshik et al. |
| 6,008,690 A | 12/1999 | Takeshima et al. |
| 6,017,354 A | 1/2000 | Culp et al. |
| 6,026,003 A | 2/2000 | Moore et al. |
| 6,048,789 A | 4/2000 | Vines et al. |
| 6,137,276 A | 10/2000 | Rudolph |
| 6,190,381 B1 | 2/2001 | Olsen et al. |
| 6,326,177 B1 | 12/2001 | Schoenbach et al. |
| 6,508,806 B1 | 1/2003 | Hoste |
| 6,831,377 B2 | 12/2004 | Yampolsky et al. |
| 6,953,460 B2 | 10/2005 | Maguire et al. |
| 7,449,021 B2 | 11/2008 | Underwood et al. |
| 7,496,401 B2 | 2/2009 | Bernabel |
| 7,669,309 B2 | 3/2010 | Johnson et al. |
| 7,767,433 B2 | 8/2010 | Kuthi et al. |
| 7,855,904 B2 | 12/2010 | Kirbie et al. |
| 7,937,143 B2 | 5/2011 | Demarais et al. |
| 8,000,813 B2 | 8/2011 | Schoenbach et al. |
| 8,216,224 B2 | 7/2012 | Morris et al. |
| 8,295,902 B2 | 10/2012 | Salahieh et al. |
| 8,512,334 B2 | 8/2013 | Nuccitelli et al. |
| 8,688,227 B2 | 4/2014 | Nuccitelli et al. |
| 8,822,222 B2 | 9/2014 | Beebe et al. |
| 9,101,337 B2 | 8/2015 | Hoegerte et al. |
| 9,101,764 B2 | 8/2015 | Nuccitelli et al. |
| 9,724,155 B2 | 8/2017 | Nuccitelli et al. |
| 9,861,802 B2 | 1/2018 | Mickelsen |
| 9,956,391 B2 | 5/2018 | Weissberg et al. |
| 10,252,050 B2 | 4/2019 | Kreis et al. |
| 10,850,095 B2 | 12/2020 | Ebbers et al. |
| 10,857,347 B2 | 12/2020 | Danitz et al. |
| 11,167,125 B2 | 11/2021 | Moss et al. |
| 11,571,569 B2 | 2/2023 | Danitz et al. |
| 2001/0003800 A1 | 6/2001 | Crowley |
| 2001/0025177 A1 | 9/2001 | Woloszko et al. |
| 2002/0193833 A1 | 12/2002 | Dimmer et al. |
| 2003/0204161 A1 | 10/2003 | Petric |
| 2003/0233087 A1 | 12/2003 | Chen et al. |
| 2004/0080964 A1 | 4/2004 | Buchmann |
| 2004/0181237 A1 | 9/2004 | Forde et al. |
| 2004/0240241 A1 | 12/2004 | Chueh et al. |
| 2004/0267254 A1 | 12/2004 | Manzo et al. |
| 2005/0119649 A1 | 6/2005 | Swanson |
| 2005/0171534 A1 | 8/2005 | Habib |
| 2006/0062074 A1 | 3/2006 | Gundersen et al. |
| 2006/0079886 A1 | 4/2006 | Orszulak et al. |
| 2006/0090723 A1 | 5/2006 | Stuart |
| 2006/0139977 A1 | 6/2006 | Oicles et al. |
| 2007/0129626 A1 | 6/2007 | Mahesh et al. |
| 2008/0031337 A1 | 2/2008 | Hasegawa et al. |
| 2008/0077189 A1 | 3/2008 | Ostroff |
| 2008/0091192 A1 | 4/2008 | Paul et al. |
| 2009/0012513 A1 | 1/2009 | Utley et al. |
| 2009/0082762 A1 | 3/2009 | Ormsby et al. |
| 2009/0131798 A1* | 5/2009 | Minar ............... A61B 5/02007 600/463 |
| 2009/0171372 A1 | 7/2009 | Mohr |
| 2009/0198231 A1 | 8/2009 | Esser et al. |
| 2009/0247944 A1 | 10/2009 | Kirschenman et al. |
| 2009/0299362 A1 | 12/2009 | Long et al. |
| 2010/0038971 A1 | 2/2010 | Sanders et al. |
| 2010/0042095 A1 | 2/2010 | Bigley et al. |
| 2010/0049194 A1 | 2/2010 | Hart et al. |
| 2010/0063496 A1 | 3/2010 | Trovato et al. |
| 2010/0198040 A1 | 8/2010 | Friedman et al. |
| 2010/0240995 A1 | 9/2010 | Nuccitelli et al. |
| 2010/0331758 A1 | 12/2010 | Davalos et al. |
| 2011/0015630 A1 | 1/2011 | Azure |
| 2011/0092973 A1 | 4/2011 | Nuccitelli et al. |
| 2011/0112527 A1 | 5/2011 | Hamilton et al. |
| 2011/0118729 A1 | 5/2011 | Heeren et al. |
| 2011/0144641 A1 | 6/2011 | Dimalanta et al. |
| 2011/0160514 A1 | 6/2011 | Long et al. |
| 2011/0270249 A1 | 11/2011 | Utley et al. |
| 2012/0158078 A1 | 6/2012 | Moulder et al. |
| 2012/0277624 A1 | 11/2012 | Cucin |
| 2012/0277763 A1 | 11/2012 | Greenblatt et al. |
| 2012/0310230 A1 | 12/2012 | Willis |
| 2013/0018441 A1 | 1/2013 | Childs |
| 2013/0190836 A1 | 7/2013 | McCreery |
| 2013/0289358 A1 | 10/2013 | Melsky et al. |
| 2013/0302409 A1 | 11/2013 | Fuchs et al. |
| 2013/0345697 A1 | 12/2013 | Garcia et al. |
| 2014/0046322 A1 | 2/2014 | Callas et al. |
| 2014/0081256 A1 | 3/2014 | Carmel et al. |
| 2014/0228835 A1 | 8/2014 | Mielekamp et al. |
| 2014/0277219 A1 | 9/2014 | Nanda |
| 2014/0336638 A1 | 11/2014 | Deem et al. |
| 2014/0364797 A1 | 12/2014 | Schoenbach et al. |
| 2015/0032100 A1 | 1/2015 | Coulson et al. |

(56) References Cited

U.S. PATENT DOCUMENTS

| | | |
|---|---|---|
| 2015/0065946 A1 | 3/2015 | Gehl et al. |
| 2015/0201991 A1 | 7/2015 | Zemlin |
| 2015/0230858 A1 | 8/2015 | Long et al. |
| 2015/0272657 A1 | 10/2015 | Yates et al. |
| 2016/0192999 A1 | 7/2016 | Stulen et al. |
| 2016/0287329 A1 | 10/2016 | Asirvatham et al. |
| 2016/0317216 A1 | 11/2016 | Hermes et al. |
| 2017/0127987 A1 | 5/2017 | Hezi-Yamit et al. |
| 2017/0197077 A1 | 7/2017 | Harpak et al. |
| 2017/0215955 A1 | 8/2017 | Hancock et al. |
| 2017/0216353 A1 | 8/2017 | Nuccitelli et al. |
| 2017/0245928 A1 | 8/2017 | Xiao et al. |
| 2017/0246455 A1 | 8/2017 | Athos et al. |
| 2017/0319851 A1 | 11/2017 | Athos et al. |
| 2017/0360502 A1 | 12/2017 | Osypka |
| 2018/0000540 A1 | 1/2018 | Ogle et al. |
| 2018/0078755 A1 | 3/2018 | Kreis et al. |
| 2018/0110557 A1 | 4/2018 | Muratori et al. |
| 2018/0154142 A1 | 6/2018 | Guo et al. |
| 2018/0243558 A1 | 8/2018 | Athos et al. |
| 2018/0296264 A1 | 10/2018 | DeSimone et al. |
| 2018/0317946 A1 | 11/2018 | Adams et al. |
| 2018/0360333 A1 | 12/2018 | Masuda et al. |
| 2019/0269904 A1 | 9/2019 | Kreis et al. |

FOREIGN PATENT DOCUMENTS

| | | | |
|---|---|---|---|
| EP | 2613723 B1 | 7/2013 | |
| WO | WO2010/107947 A1 | 9/2010 | |
| WO | WO2011/146498 A2 | 11/2011 | |
| WO | WO2013/058089 A1 | 4/2013 | |
| WO | WO2013/143603 A1 | 10/2013 | |
| WO | WO2013/154775 A1 | 10/2013 | |
| WO | WO-2013154775 A1 * | 10/2013 | ............. A61B 18/14 |
| WO | WO2014/060854 A1 | 4/2014 | |
| WO | WO2015/120190 A1 | 8/2015 | |
| WO | WO2016/089781 A1 | 6/2016 | |
| WO | WO2017/200954 A1 | 11/2017 | |
| WO | WO2017/201394 A1 | 11/2017 | |
| WO | WO2018/075946 A1 | 4/2018 | |
| WO | WO2018/089506 A1 | 5/2018 | |
| WO | WO2018/106672 A1 | 6/2018 | |
| WO | WO2018/178252 A1 | 10/2018 | |
| WO | WO2020/168214 A1 | 8/2020 | |

OTHER PUBLICATIONS

Anand et al.; Adaptive immune response to nano-pulse stimulation (NPS); Nov. 11, 2016, Poster presentation at the 31st Annual Meeting and Associated Programs of the Society for Immunotherapy of Cancer; 1 page; retreived rom the internet (http://pulsebiosciences.com/assets/Pulse%20AIR%20poster.pdf); on Mar. 13, 2018.

Baker et al.; Stacking power Mosfets for use in high speed instrumentation; Review of scientific instruments; 63(12; pp. 5799-5801; Dec. 1992.

Beebe; Hepatocellular carcinoma ablation and possible immunity in the age of nanosecond pulsed electric fields; Journal of Hepatocellular carcinoma; No. 2; pp. 49-55; May 2015.

Bhosale et al.; Design and Simulation of 50 kV, 50 A Solid State Marx Generator; International Conference on Magnetics, Machines & Drives (AICERA—2014 iGMMD), IEEE; pp. 1-5; Jul. 24, 2014.

Carey et al.; Marx Generator Design and Performance; IEEE; InPower Modulator Symposium, 2002 High-Voltage Workshop; Conference Record of the Twenty-Fifth International; Applied Physical Electronics, Austin TX; 4 pages; Jun. 2002.

Casey et al.; Solid-State Marx Bank Modulator for the Next Generation Linear Collider; Conference Record of the 26th; IEEE; International Power Modulator Symposium and 2004 High Voltage Workshop (PMC), San Francisco, California; pp. 257-260; May 23-26, 2004.

Cook et.al.; Design and Testing of a Fast, 50 kV Solid-State Kicker Pulser; IEEE; Inconference record of the International Power Modulator Symposium 2002; pp. 106-109; Lawrence Livermore National lab; 6 pages; Jun. 24, 2002.

European Supplemental Search Report dated Mar. 21, 2022 for European Patent Application No. 20756431.1; 7 pages.

Final Office action dated Jul. 5, 2019 for U.S. Appl. No. 15/269,273; 12 pages.

Garon et al.; In Vitro and In Vivo Evaluation and a Case Report of Intense Nanosecond Pulsed Electric Field as a Local Therapy for Human Malignancies; International Journal of Cancer; 121(3); pp. 675-682; Aug. 2007.

Gaudreau et al; Solid-State Pulsed Power Systems for the Next Linear Collider; IEEE; InPulsed Power Plasma Science, 2001, PPPS-2001. Digest of Technical Papers; vol. 1; pp. 298-301; Jun. 17, 2001.

Gundersen et al.; Nanosecond pulse generator using a fast recovery diode: IEEE; InProceedings of the 26th Inernational Pulsed Modulator Conference; 603-606; (year of pub. sufficiently earlier than effective US filing date and any foreign priority date) 2004.

International Search Report and Written Opinion dated Dec. 11, 2018 for PCT/US2018/045433; 16 pages.

International Search Report and Written Opinion dated Jun. 22, 2020 for PCT/US2020/018321; 18 pages.

International Search Report dated Feb. 27, 2018 for PCT/US2017/057698; 5 pages.

International Search Report dated Mar. 22, 2018 for PCT/US2017/064685; 6 pages.

International Search Report dated May 22, 2018 for PCT/US2018/019213; 4 pages.

Jiang et al.; Marx Generator Using Power Mosfets; IEEE; InPulsed Power Conference, PPC/09; pp. 408-410; Jun. 28, 2009.

Kirbie et al.; An All Solid State Pulse Power Source for High PRF induction Accesieratiors; InPower Modulator Symposium, 1988; Conference Record of the 1988 Twenty-Third International, Rancho Mirage, CA.; ; pp. 6-11; 6 pages; Jun. 22-25, 1998.

Krasnykh et al.; A Solid State Marx Type Modulator for Driving a TWT; Conference Record of the 24th International Power Modulator Sypolsium 2000; pp. 209-211; Jun. 26, 2000.

Mcdaniel et al., Nanosecond pulsed electric field treatment of tumor cell lines triggers immunogenic cell death (ICD); Nov. 11, 2016, Poster presentation at the 31st Annual Meeting and Associated Programs of the Society for Immunotherapy of Cancer (SITC 2016), National Harbor, MD, USA; 1 page; retrieved from the Internet (http://pulsebiosciences.com/assets/Pulse%20ICD%20poster.pdf) on Mar. 13, 2018.

Mcdaniel et al.; P329 Nanosecond pulsed electric field treatment of tumor cell lines triggers immunogenic cell death (ICD); Journal for ImmunoTherapy of Cancer: 31st Annual Meeting and Associated Programs of the Society for Immunotherapy of Cancer (SITC 2016): part two: National Harbor, MD, USA, p. 175; Nov. 16, 2016.

Non Final Office Action dated Dec. 26, 2018 for U.S. Appl. No. 15/269,273; 8 pages.

Okamura et al.; Development of the High Repetitive impulse Voltage Generator Using Semiconductor Switches; IEEE; InPulsed Power Conference; Digest of Technical Papers, 12 th IEEE International; vol. 2; pp. 807-810; Jun. 27, 1999.

Preliminary Report on Patentability dated Mar. 19, 2019 for PCT/US2017/052340; 6 pages.

Redondo et al.; Solid-State Marx Generator Design with an Energy Recovery ReseS Circuit for Output Transformer Association; InPower Electronics Speialists Conference, 2007, PESC, IEEE 2007; pp. 2987-2992; (5 pages); Jun. 17, 2007.

Richter-Sand et al.; Marx-Stacked IGBT Modulators for High Voltage. High Power Applications; IEEE; InPower Modulator Symposium, 2002 and 2002 High-Voltage Workshop., Conference Record of the Twenty-Fifth International 2002; pp. 390-393; Jun. 30, 2002.

Sack et al.; Design Considerations for a Fast Stacked-MOSFET Switch; IEEE Transactions on Plasma Science; 41(10); pp. 2630-2636; Oct. 2013.

Tang et al.; Diode Opening Switch Based Nanosecond High Voltage Pulse Generators for Biological and Medical Applications; IEEE Transactions on Dielectrics and Electrical Insulation, 14(4); pp. 878-883; Aug. 2007.

(56) References Cited

OTHER PUBLICATIONS

Wang et al.; Solid-State High Voltage Nanosecond Pulse Generator; IEEE InPulsed Power Conference;pp. 1199-1202; 4 pages; Jun. 13, 2005.
Yao et al.; FPGA-Controlled All-Solid-State Nanosecond Pulse Generator for Biological Applications; IEEE Transactions on Plasma Science; 40(10; pp. 2366-2372; Oct. 2012.
Yatim et al.; RIPK1 and NF-xB signaling in dying cells determines cross-priming of CD8+T cells; Science; 350(6258); pp. 328-334; Oct. 16, 2015.

* cited by examiner

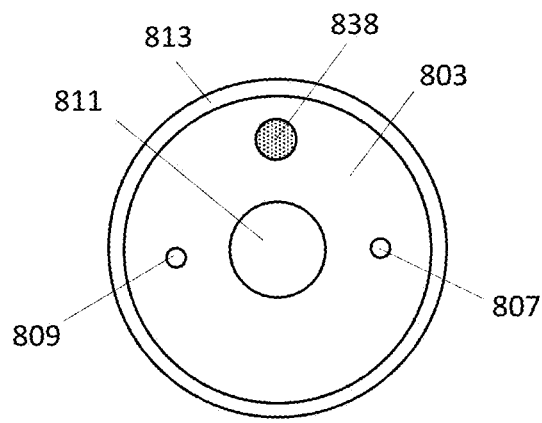
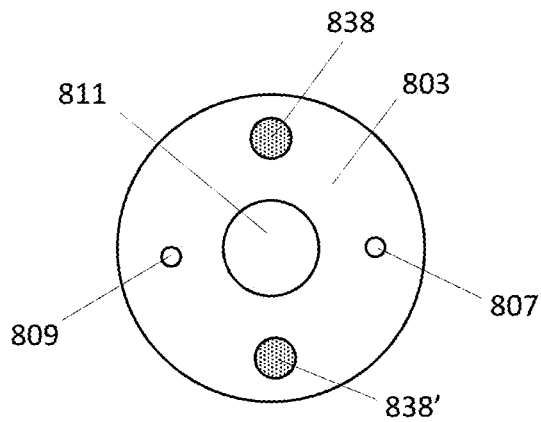
FIG. 8A  FIG. 8B
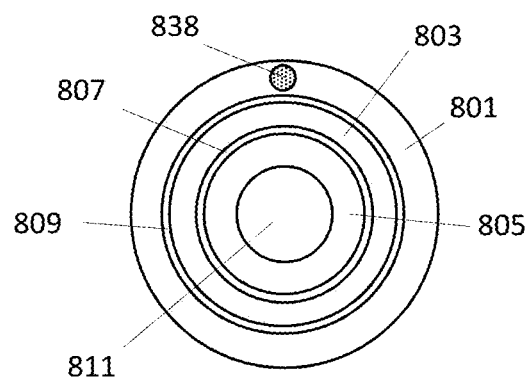
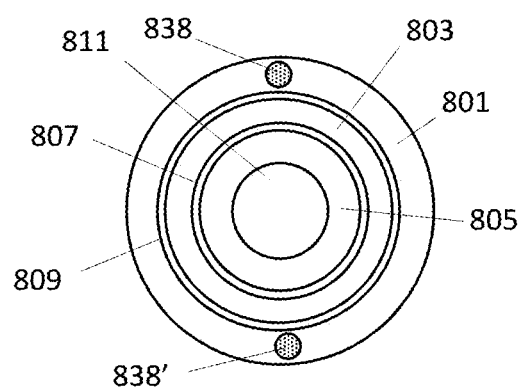
FIG. 8C  FIG. 8D

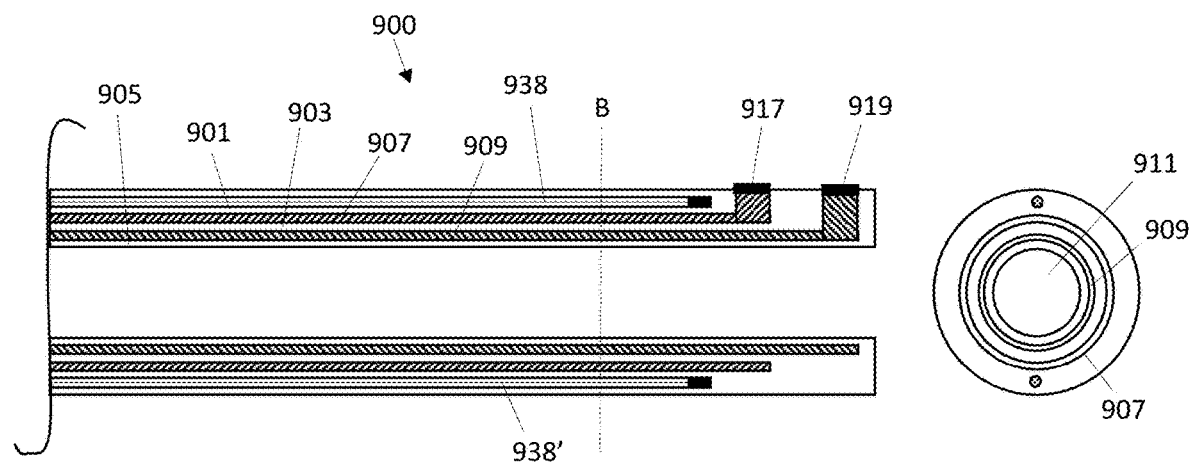
FIG. 9A   FIG. 9B
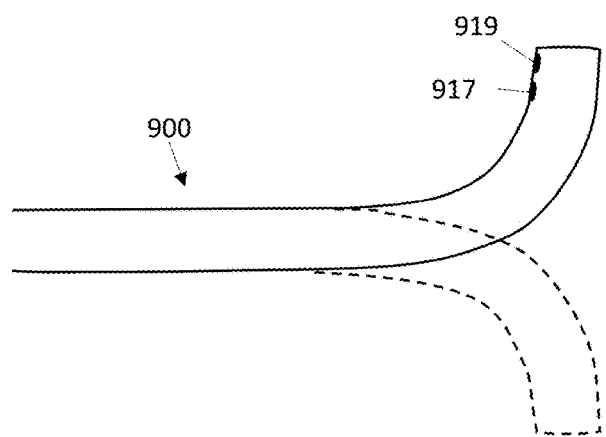
FIG. 9C

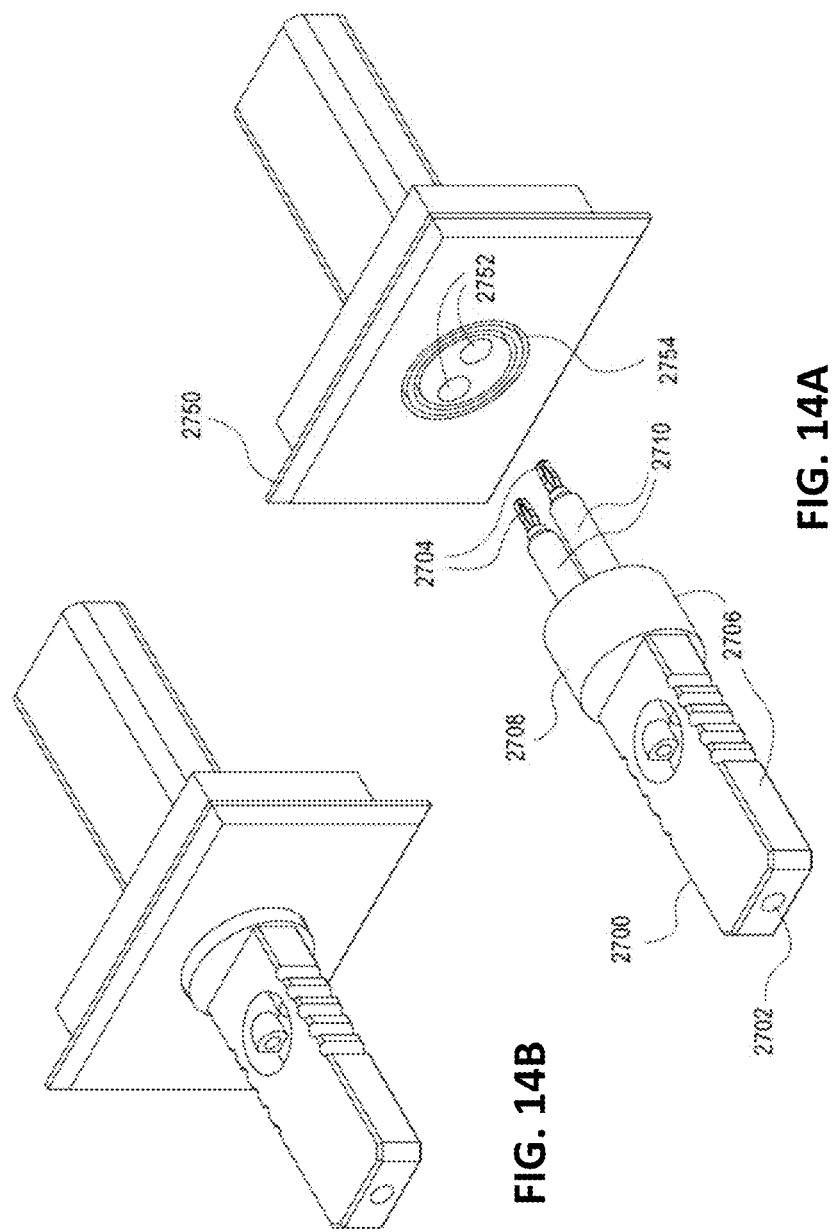

DETAIL H

TREATING TISSUE PULSED ENERGY USING HIGH-VOLTAGE CATHETERS

CROSS REFERENCE TO RELATED APPLICATIONS

This patent application is a divisional of U.S. patent application Ser. No. 16/789,350, filed on Feb. 12, 2020, titled "HIGH-VOLTAGE CATHETERS FOR SUB-MICROSECOND PULSING," now U.S. Pat. No. 11,571,569, which claims the benefit of U.S. Provisional Patent Application No. 62/806,750, filed on Feb. 15, 2019, titled "HIGH-VOLTAGE CATHETERS FOR SUB-MICROSECOND PULSING," each of which are incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses (e.g., devices, systems, etc.) and methods that may be used to perform medical operations to treat patients. Specifically, the apparatuses described herein can include minimally invasive devices, such as catheters, endoscopes, laparoscopes, etc. that may apply high-voltage, short electrical pulses to treat patients.

BACKGROUND

Short, high-field strength electric pulses have been described for electroperturbation of biological cells. For example, electric pulses may be used in treatment of human cells and tissue including tumor cells, such as basal cell carcinoma, squamous cell carcinoma, and melanoma. The voltage induced across a cell membrane may depend on the pulse length and pulse amplitude. Pulses longer than about 1 microsecond may charge the outer cell membrane and lead to opening of pores. Permanent openings may result in instant or near instant cell death. Pulses shorter than about 1 microsecond may affect the cell interior without adversely or permanently affecting the outer cell membrane and result in a delayed cell death with intact cell membranes. Such shorter pulses with a field strength varying in the range of 10 kV/cm to 100 kV/cm may trigger apoptosis (i.e. programmed cell death) in some or all of the cells exposed to the described field strength and pulse duration. These higher electric field strengths and shorter electric pulses may be useful in manipulating intracellular structures, such as nuclei and mitochondria. For example, sub-microsecond (e.g., nanosecond) high voltage pulse generators have been proposed for biological and medical applications.

Because of the very high therapeutic voltages, as well as the very fast pulse times, applicators for delivery of such nanopulse energy devices must be configured so as to avoid damaging tissues or otherwise harming the patient. The risks of delivering high-voltage energy, such risks including electrical shock, arcing, burns, internal-organ damage, and cardiac arrhythmias, are even more acute when the high-voltage device is intended to be inserted into the body.

Thus, it would be beneficial to provide devices, such as catheters, endoscopes, laparoscopes, etc. that may apply high-voltage, short (also referred to as "fast") electrical pulses to treat patients while addressing the above-mentioned risks.

SUMMARY OF THE DISCLOSURE

Described herein are apparatuses (including systems and devices, such as catheters, endoscopes, laparoscopes, etc.) and methods for the treatment of a patient that may use them to more effectively apply therapeutic energy, including but not limited to short, high field strength electric pulses, while avoiding the risk of arcing or otherwise harming the tissue. These applicators may be particularly well suited, for example, for treatments of various disorders and diseases, such as, but not limited to cancer (and other types of abnormal tissue growth), and the like. These applications may be also particularly well suited for use with various fully and partially automated systems, such as robotic systems.

In particular, the apparatuses described herein may be configured as single-use catheters that can be used with a variety of different re-usable generator systems, as will be described in greater detail herein.

Furthermore, the apparatuses described herein may be integrated into systems that are configured to be mounted onto or coupled to a robotic arm of a robotic system, such as robotic medical treatment system or robotic surgical system. While for convenience of description the present disclosure may refer to the robotic surgical system, however, it should be understood that such robotic surgical system is intended to cover any robotic medical treatment system (including for cosmetic applications) and may include robotic systems having guidance. In some variations instruments can be guided and controlled by the robotic surgical system during a surgical procedure. For example, the devices described herein may be used through one or more operating channels of a robotic system. Examples of robotic systems that may be modified for use as described herein (and/or may be used with or may include any of these features) are described in U.S. patent application Ser. No. 15/920,389 "TREATMENT INSTRUMENT AND HIGH-VOLTAGE CONNECTORS FOR ROBOTIC SURGICAL SYSTEM," filed on Mar. 13, 2018, which is hereby incorporated by reference in its entirety for all purposes.

According to one aspect, apparatuses described herein comprise catheters and scopes (e.g., endoscopes, laparoscopes, etc.) that may include a tip having a plurality of electrodes that may be retractable and/or may include a retractable/removable insulating region that may protect and insulate one or more treatment electrodes (e.g., plate electrodes, needle electrodes, etc.) through which high-voltage rapidly pulsed energy may be delivered into the tissue. These apparatuses may be configured safely and reliably to deliver microsecond or sub-microsecond (e.g., nanosecond, picosecond, etc.) pulses, and may include an electric field with a sub-microsecond pulse width of between 0.1 nanoseconds (ns) and 1000 nanoseconds, or shorter, such as 1 picosecond, which may be referred to as sub-microsecond pulsed electric field. This pulsed energy may have high peak voltages, such as 1 kilovolts per centimeter (kV/cm), 2-3 kV/cm, 5 kV/cm, 10 kV/cm, 20 kV/cm, 50 kV/cm, to 500 kV/cm. Treatment of biological cells may use a multitude of periodic pulses at a frequency ranging from 0.1 per second (Hz) to 10,000 Hz, and may trigger apoptosis, for example, in the diseased tissue or abnormal growth, such as cancerous, precancerous or benign tumors. Selective treatment of such tumors with high-voltage, sub-microsecond pulsed energy can induce apoptosis within the tumor cells without substantially affecting normal cells in the surrounding tissue due to its non-thermal nature. A subject may be a patient (human or non-human, including animals). A user may operate the apparatuses described herein on a subject. The user may be a physician (doctor, surgeon, etc.), medical technician, nurse, or care provider.

Thus, the application of high-voltage, fast (e.g., microsecond, nanosecond, picosecond, etc.) electrical pulses may include applying a train of sub-microsecond electrical pulses having a pulse width, for example, of between 0.1 nanoseconds (ns) and 1000 nanoseconds. Applying high-voltage, fast electrical pulses may include applying a train of sub-microsecond electrical pulses having peak voltages of between, for example, 1 kilovolts per centimeter (kV/cm) and 100 kV/cm. Applying high-voltage, fast electrical pulses may include applying a train of sub-microsecond electrical pulses at a frequency, for example, of between 0.1 per second (Hz) to 10,000 Hz.

For example, described herein are apparatuses for treating tissue. For example, these apparatuses may include: an elongate body comprising: a first conductive layer formed from a first plurality of braided or woven filaments extending down at least a portion of the length of the elongate body; a second conductive layer formed from a second plurality of braided or woven filaments extending concentric to the first conductive layer; wherein the first and second conductive layers are enclosed by a flexible electrically insulating material; a first electrode at a distal end region of the catheter in electrical communication with the first conductive layer; a second electrode at the distal end region of the catheter in electrical communication with the second conductive layer; and a high-voltage connector adapted to couple the first and second conductive layers to a pulse generator.

Any of these apparatuses may include one or more lumens. For example the apparatuses described herein may include a guidewire lumen that is concentrically surrounded by the first and second conductive layers. The guidewire lumen may be configured to fit any standard guidewire (or guide catheter). The guidewire lumen may include a lubricious coating or cover (e.g., Teflon). This lumen may also or alternatively be configured as a working channel for passing one or more additional instruments. The same or other (e.g., additional) lumen may be used for any other purpose, including visualization (e.g., deploying a fiber optic, camera, etc.), delivery and/or removal of material (drug, conductive gel, saline, conducive fluid, etc.), vacuum, etc. For example, in some variations a lumen extending the length of the apparatus may deliver conductive fluid and/or gel to the region at or around the electrodes. In some variations the outlet for the lumen may be positioned at or near the electrodes; for example the outlet(s) of the one or more lumen configured to carry conductive fluid may be positioned adjacent to (around, beside, and/or between) the one more electrodes on the apparatus.

These apparatuses may be configured as catheters. Some embodiments of the present disclosure provide an advantageous and unique combination of a concentric configuration, a plurality of layers and an ability to withstand high voltages, which provides flexibility desired for the catheters while accommodating size limitations or geometric constrains, improving safety and minimizing noise.

The first and second electrodes may be separated by 0.5 mm or more (e.g., 0.8 or more, 1 mm or more, 2.0 mm or more 3.0 mm or more 3.2 mm or more 3.5 or more, 4 mm or more, 4.5 mm or more, 5 mm or more, 6 mm or more, etc.).

In general, the first and second conductive layers are configured to conduct high-voltage, fast pulses of electrical energy. The first and second conductive layers may also be configured to modify the mechanical properties of the catheter. For example, the first conductive layer may comprise a first braid pattern of conductive filaments that varies along a distal to proximal length of the catheter so that the catheter is more flexible at the distal end. For example, the braided pattern may have a different braid angle along the length of the catheter. In some variations the braid angle may increase along the proximal-to-distal length; in some variations the braid angle may decrease along the proximal-to-distal length. The braid angle may vary constantly or by one more steps. In some variations, the second conductive layer comprises a second braid pattern of conductive filaments that also varies along the distal to proximal length of the catheter. In some variations the pattern of filaments in the first conductive layer is different than the pattern of filaments in the second conductive layer. For example, the pattern of braided or woven filaments in the first conductive layer may be a mirror image of the pattern of braided or woven filaments in the second conductive layer.

Any of the apparatuses described herein may include a bias (e.g., on an outer surface of the distal end region of the apparatus) that is configured to drive the distal end region of the catheter against a vessel wall when deployed in a vessel. Any appropriate bias may be used (e.g., spring, such as a leaf spring, coil spring, etc., an inflatable balloon, a shape-memory alloy, etc.).

The flexible insulating material may have a dielectric strength sufficient to withstand 1 or 2 kV or more, 3 kV or more, 5 kV or more (e.g., 7 kV or more, 8 kV or more, 9 kV or more, 10 kV or more, 12 kV or more, 15 kV or more, etc.). More than one flexible insulating material (e.g., having different dielectric strengths) may be used; including as use in different regions, such as around the first and second (or more) conductive layers. For example, the first and second conductive regions may be surrounded by a high dielectric strength material than other portions of the catheter.

Any of these apparatuses (e.g., catheters) may include one or more steering tendons (or wires) within a lumen of the elongate body. The tendons may be fixed at one end region (e.g., to the distal end region of the guidewire) and otherwise free to move within a lumen in the body of the apparatus.

The apparatuses described herein may include any appropriately configured electrodes, including one or more of: needle electrodes, plate electrodes, ring electrodes, surface electrodes, knife electrodes, etc. The electrodes may be static (e.g., present on the surface or configured to extend from the surface) and/or they may be dynamic (e.g., configured to extend from the body of the device and/or retract into the device). For example, the first and second electrodes comprise needle electrodes. The electrodes may be positioned on a distal end face of the apparatus (e.g., catheter) and/or they may be positioned on a lateral side of the elongate body.

In some variations a system for treating tissue may include: a catheter comprising: an elongate body having a first conductive layer formed from a first plurality of filaments extending down at least a portion of the length of the elongate body, a second conductive layer formed from a second plurality of filaments extending concentric to the first conductive layer, wherein the first and second conductive layers are enclosed by a flexible insulating material having a dielectric strength sufficient to withstand 1 kV or more, for example, 5 kV or more; a first electrode at a distal end region of the catheter in electrical communication with the first conductive layer; a second electrode at the distal end region of the catheter in electrical communication with the second conductive layer; and a high-voltage connector adapted to couple the first and second conductive layers to a pulse generator configured to generate a plurality of electrical pulses having amplitude of at least 0.1 kV and a duration of less than 1000 nanoseconds.

Any of the apparatuses or systems may include a pulse generator. For example, also described herein are systems for treating tissue, the system comprising: a catheter comprising: an elongate body having a first conductive layer formed from a first plurality of filaments extending down the length of the elongate body, a second conductive layer formed from a second plurality of filaments extending concentric to the first conductive layer, wherein the first and second conductive layers are enclosed by a flexible insulating material having a dielectric strength sufficient to withstand 1 kV or more; a first electrode at a distal end region of the catheter in electrical communication with the first conductive layer; a second electrode at the distal end region of the catheter in electrical communication with the second conductive layer; a pulse generator configured to generate a plurality of electrical pulses having amplitude of at least 0.1 kV and a duration of less than 1000 nanoseconds; and a high-voltage connector configured to connect to the pulse generator through a port, the high-voltage connector adapted to couple the first and second conductive layers to the pulse generator. Examples of pulse generators that may be modified or use as described herein are shown, for example in U.S. patent application Ser. No. 15/269,273 "HIGH VOLTAGE CONNECTORS AND ELECTRODES FOR PULSE GENERATORS," filed on Sep. 19, 2016, which is hereby incorporated by reference in its entirety for all purposes.

Also described herein are methods of using any of the apparatuses (e.g., catheters), for example, to treat tissue. Generally these catheters may be configured to treat tissue within a body by delivering, through the catheter, one or a train of high-voltage, fast (e.g., sub-millisecond, nanosecond, picosecond) pulses. For example, the catheters and systems of the present disclosure may be used in various cardiac applications, esophageal applications, methods of treatment of the lung tissue, or bronchial passages. Also, the methods of the present disclosure include the methods of therapeutic treatment, including cosmetic treatments. In general, a cosmetic treatment may include treatment of skin or other tissue within a body. Cosmetic treatments may be applied to change or enhance a user's appearance. Although many of the examples described herein are specific to methods of treatment (including cosmetic methods) the methods described herein may be used for non-treatment purposes, including testing of the catheter, experimental purposes (e.g., inserting the catheter into a model of a body), etc.

For example, described herein are methods of treating tissue, the method comprising: inserting a distal end of a catheter into a body, wherein the catheter comprises at least two electrodes at a distal end region; applying a plurality of electrical pulses having an amplitude of greater than 0.1 kV and a duration of less than 1000 nanoseconds to a proximal end of the catheter through a first plurality of filaments extending at least partially down the length of the catheter and through a second plurality of filaments extending at least partially down the length of the catheter; and delivering the applied plurality of electrical pulses to the body from a first electrode of the at least two electrodes in electrical communication with the first plurality of filaments and a second electrode of the at least two electrodes in electrical communication with the second plurality of filaments, wherein the first and the second plurality of filaments is configured and insulated to withstand 1 kV or more. The second plurality of filaments may extend concentrically over the first plurality of filaments. In some embodiments, the first and the second plurality of filaments may be configured and insulated to withstand 2 kV or more, 3 kV or more, 5 kV or more, or 9 kV or more.

Also described herein are methods of delivering pulsed power to any of the apparatuses described herein, including in particular to a catheter. For example, a method may include: connecting a high-voltage connector to a first conductive layer and a second conductive layer of a catheter, the first conductive layer formed from a first plurality of filaments extending down at least a portion of a length of an elongate body of the catheter, the second conductive layer formed from a second plurality of filaments extending concentric to the first conductive layer; and applying a plurality of electrical pulses having an amplitude of 1 kV or more from the high-voltage connector through the first plurality of filaments and through the second plurality of filaments, wherein the first and second conductive layers are insulated by a flexible insulating material having a dielectric strength sufficient to withstand 1 kV or more. In some embodiments the electrical pulses may have an amplitude of between 1 kV and 15 kV, or between 1 kV and 9 kV, or between 3 kV and 5 kV, or any sub-range within the above ranges.

Any of these methods may also include connecting the catheter to a pulse generator using a high-voltage connector. The high voltage connector may include a lip, rim, skirt, ridge, etc. and/or a standoff region. In some variations the high-voltage connector may include one or more interlocks configured to prevent energy from being applied through the connector until sealing contact is ensured (e.g., by applying a low-power signal through and determining the stability of the connection, e.g., via impedance or other electrical property.

Inserting may comprise inserting the catheter over a guide wire using a guide wire lumen passing concentrically through the first and second plurality of filaments, for example, braided or woven filaments. The guidewire may be used to guide (position) the catheter, for example, to a location within a body.

Any of these methods may also include driving the distal end of the catheter against the tissue so that the first and second electrodes contact the tissue. For example, driving may include inflating an inflatable balloon on a side of the distal end of the catheter.

As described above, at least one or both of the first and second plurality of filaments may comprise braided or woven filaments. The arrangement of the first and second plurality of filaments may be configured to reduce loop currents (electrical field leakage).

The methods described herein may include checking impedance between a first electrode (e.g., at a distal end region of the catheter) in electrical communication with the first conductive layer and a second electrode (e.g., at the distal end region of the catheter) in electrical communication with the second conductive layer. The impedance may be checked or monitored either prior to and/or while applying the plurality of electrical pulses. The impedance may be used to control operation of the apparatus and in particular the impedance may be used to turn on and/or off the application of electrical energy to the apparatus. For example, any of these methods may include periodically or continuously checking impedance between the first and second electrodes during the application of the plurality of electrical pulses and stopping or suspending the application, for example, if the impedance falls below an impedance threshold or, alternatively, exceeds an impedance threshold, or suspending application of electrical pulses until the impedance exceeds an impedance threshold.

The apparatuses and methods described herein are generally configured for bipolar operation, e.g., wherein the apparatus includes two or more (e.g., groups) of electrodes between which the electrical energy is applied to generate a therapeutic electric field, as described herein. However, in some variations the apparatuses and devices described herein may be configured to be operated as monopolar devices in which a single electrode (or group of electrodes) is used to apply energy from the device, and the electrical return is a remote one or more electrodes, including a second apparatus, an external electrode, such as an electrical patch or pad. In some variations the apparatuses descried herein may be configured to apply electrical energy between a first electrode or group of electrodes on an apparatus (e.g., catheter apparatus as described herein) and a remote electrode or group of electrodes. Any of the apparatuses described herein may be operated as a monopolar apparatus even where multiple electrodes are included, for example, by operating multiple electrodes as a group (e.g., electrically connecting their outputs).

BRIEF DESCRIPTION OF THE DRAWINGS

The novel features of the present disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 8A-8D show examples of catheters (shown in cross-section) including one (FIGS. 8A and 8C) or more (FIGS. 8B and 8D) steering tendons or pull wires.

FIGS. 9A and 9B show another example of a high-voltage catheter in longitudinal section (FIG. 9A) and in cross-section (FIG. 9B) including a pair of steering tendons on opposite sides of the catheter.

FIG. 9C shows the catheter of FIGS. 9A and 9B being steered.

FIG. 14A and FIG. 14B show examples of high-voltage connectors configured to be mated with a housing of a pulse generator (shown as a cutaway portion), before mating (FIG. 14A) and after mating (FIG. 14B).

DETAILED DESCRIPTION

Described herein are flexible catheters adapted to be inserted into a body to deliver high-voltage, fast (e.g., microsecond, nanosecond, picosecond, etc.) electrical energy to target tissue. Apparatuses and systems described herein are especially useful in high-voltage sub-microsecond pulsing applications. Therefore, for convenience of description, these catheters will be described herein, by example, in reference to high-voltage, sub-microsecond catheters.

Figure 1:
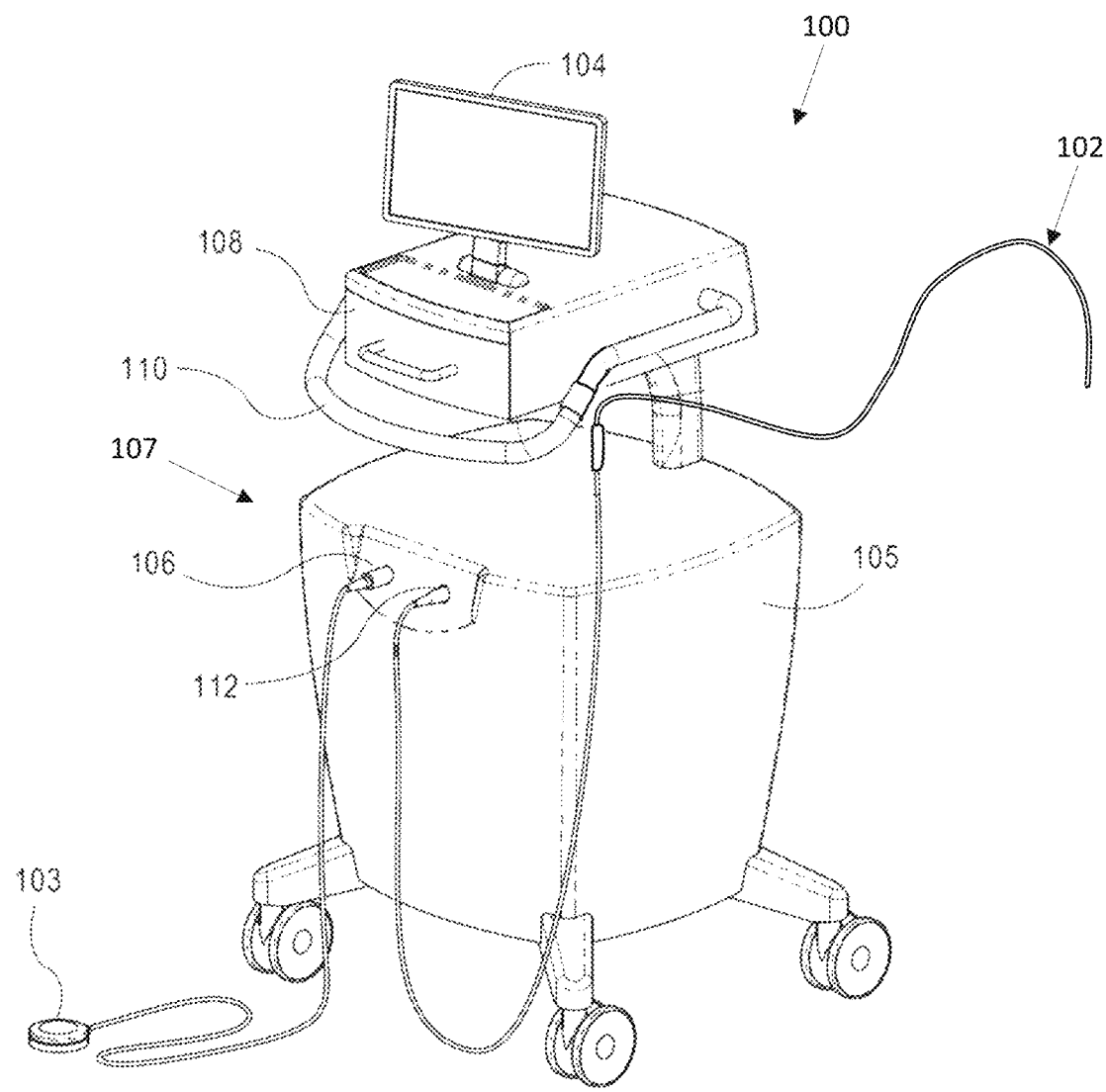
FIG. 1 schematically illustrates one example of a system, including a catheter, for delivery of high-voltage, fast pulsed electrical energy.

FIG. 1 illustrates one example of a system 100 for delivering high-voltage, fast pulses of electrical energy that includes a catheter 102 and a pulse generator 107, footswitch 103, and user interface 104. Footswitch 103 is connected to housing 105 (which may enclose the electronic components) through connector 106. The catheter 102 may include the electrodes and is connected to housing 105 and the electronic components therein through a high voltage connector 112. The high-voltage system 100 may also include a handle 110 and storage drawer 108. The system 100 may also include a holder (e.g., holster, carrier, etc.—not shown) which may be configured to hold the catheter 102.

A human operator may input a number of pulses, amplitude, pulse duration, and frequency information, for example, into a numeric keypad or a touch screen of interface 104. In some embodiments, the pulse width can be varied. A microcontroller may send signals to pulse control elements within system 100. In some embodiments, fiber optic cables allow control signaling while also electrically isolating the contents of the metal cabinet with generation system 100, e.g., the high voltage circuit, from the outside. In order to further isolate the system, system 100 may be battery powered instead of from a wall outlet.

Figure 2:
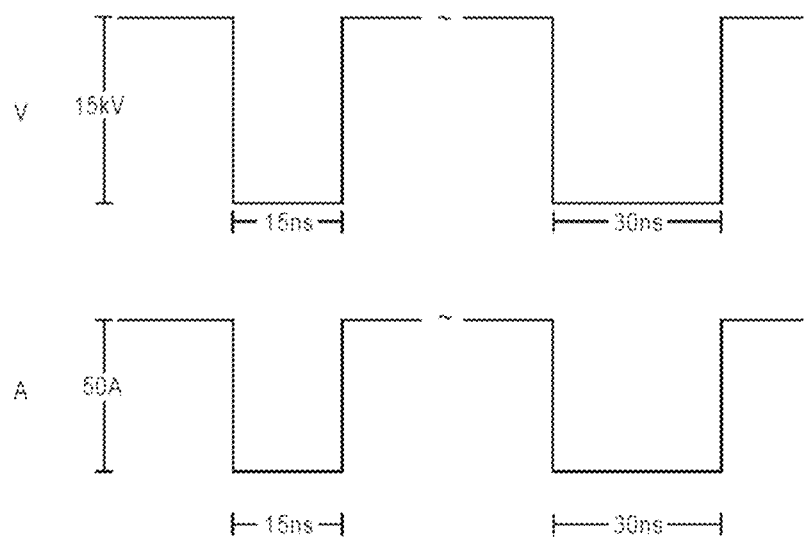
FIG. 2 illustrates an example of a pulse profile for voltage and current that may be applied by the apparatuses described herein.

FIG. 2 illustrates an example of a pulse profile for both voltage and current for a high-voltage, fast (e.g., sub-microsecond) pulsing. FIG. 2 illustrates examples of output from the system 100 with voltage shown in the top portion of the figure and the current shown on the bottom portion of the figure, showing a first and second pulses. The first pulse has an amplitude of about 15 kV, a current of about 50 A, and a duration of about 15 ns. The second pulse has an amplitude of about 15 kV, a current of about 50 A, and a duration of about 30 ns. Thus, in some examples, 15 kV may be applied to electrodes connected to the system having 4 mm between the plates so that the target tissue experiences 37.5 kV/cm (e.g., 15 kV/0.4 cm), and current between 12 and 50 A. Given a voltage, current depends heavily on the electrode type and tissue resistance.

While FIG. 2 illustrates one specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 µs, about 2 µs, about 3 µs, about 4 µs, about 5 µs, or greater than 5 µs. In addition, in some embodiments the pulses may alternate from a positive amplitude to a negative amplitude in a biphasic manner, for example, the first pulse could be +1 kV followed by second pulse at −1 kV, or a first pulse at +3 kV followed by a second pulse at −2 kV.

Figures 3A, 3B:
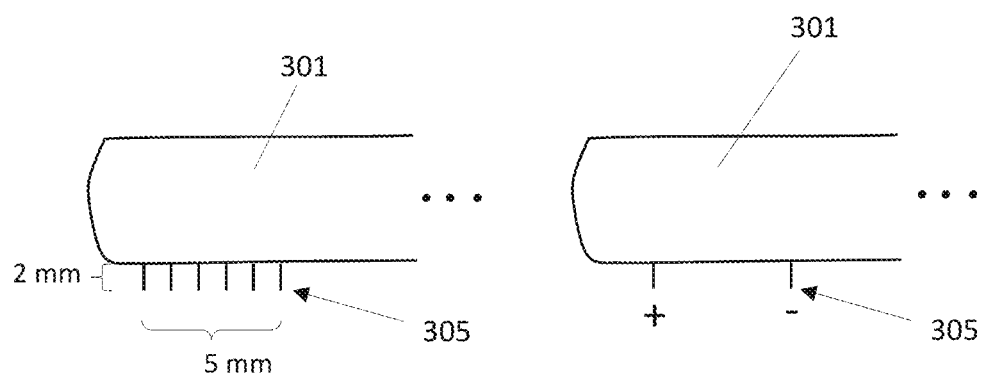
FIGS. 3A and 3B schematically illustrate examples of electrodes arranged to deliver high-voltage (e.g., 15 kV), fast (e.g., sub-millisecond) pulses of electrical energy into a tissue from the distal end of a catheter.

FIGS. 3A and 3B schematically illustrate examples of electrodes shown at the distal end of a catheter 301 (shown as perpendicularly extending or extendable needle or knife electrodes that may penetrated into the tissue. In FIG. 3A, the exemplary electrode extends 2 mm from the catheter into the tissue and form a row that is 5 mm long. More than one row of electrodes (arranged, e.g., in the long axis of the catheter and/or at an angle, including 90 degrees to the long axis) may be included. For example, multiple (e.g., two, three, etc.) rows of electrodes, e.g., 0.5 mm long electrodes, 1 mm long electrodes, 1.5 mm long electrodes, 2 mm long electrodes, etc. may be provided. Further, the space between electrodes may be shorter or longer than 1 mm (e.g., 0.5 mm, 1 mm, 1.5 mm or longer, 2 mm or longer, 2.5 mm or longer, 3 mm or longer, 3.5 mm or longer, 4 mm or longer, 4.5 mm or longer, 5 mm or longer, etc.). For example, FIG. 3B shows an example of a catheter 301 having a pair of extending/extendable electrodes 305 that are separated by 5 mm or more. In some variations the electrodes may be separated by an insulting barrier (border, ring, etc.) between, around and/or adjacent to the electrodes.

In some variations the apparatus may be configured for monopolar operation and may include just a single electrode (not shown) or may electrically couple multiple electrodes. For example, in FIG. 3A, the protruding electrodes 305 may act as a single pole (e.g., single electrode). Thus, any of these apparatuses may be used with a remote electrode (a return or electrical ground electrode, not shown). For example, in some variations the remote electrode (electrical return) may be a grounding pad on which a subject (e.g., patient) may lie. The grounding pad (or external ground) may be a conductive mesh. In general, a grounding pad may be of any appropriate material(s). Alternatively, in some variations the remote electrical return may be applied to an outer surface of the body or within the body in another location or region. Thus, any of the apparatuses and systems described herein, including the sub-microsecond pulsed, high voltage apparatuses, may be monopolar, or may be applied between separate devices. Thus, although relatively high fields may be generated between the source electrode, e.g., on an apparatus as described herein, and a return electrode, such as a ground pad, surface (e.g., skin) electrode and/or second device (e.g., a different catheter device).

When the device is operated in a monopolar configuration the resulting field may be directed or steered by positioning the return electrode so that target tissue region is between the electrode on the apparatus and the ground electrode. In some cases the target tissue region may be adjacent to the electrode on the apparatus. For example, in some variations the methods and apparatuses described herein may be used to treat a cardiac tissue, such as an epicardial, endocardial, and/or pericardial tissue. In one monopolar embodiment, the apparatus, such as a catheter apparatus with a first electrode, may be positioned within the heart (e.g., at or near the target region of the heart) and the return electrode may be a ground pad, for example, a pad that the subject is lying on. In another monopolar embodiment the apparatus with the first electrode (or a group of electrodes) may be positioned within the heart and the return electrode may be positioned on the subject's skin, e.g., above the heart, below the heart, or other remote location, in order to direct the field between the electrodes on the catheter and the return electrode, through the target tissue.

Any of the apparatuses described herein may also be used for catheter-to-catheter treatments, in which the first catheter including one or more (grouped) electrodes, as described herein, and a second (return) catheter including one or more (grouped) electrodes may be positioned on an opposite side of the target region of the tissue. For example, a cardiac treatment may include positioning a first catheter apparatus as described herein in a first chamber of the heart and a second catheter apparatus as described herein in a second chamber of the heart, and applying energy to generate a therapeutic field between the two, e.g., passing through the target tissue (e.g., a septal wall).

Figure 3C:
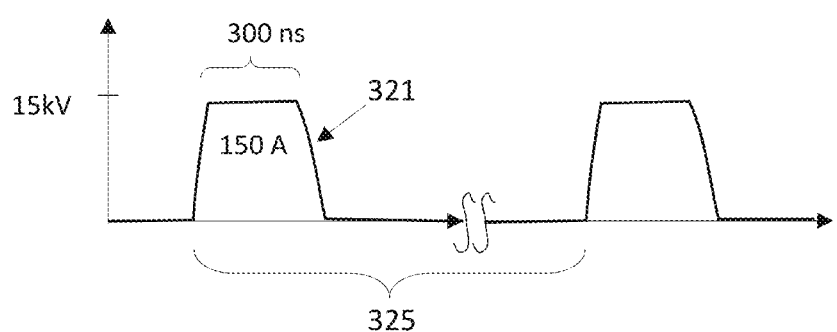
FIG. 3C illustrates one example of voltage versus time chart for a system delivering fast electrical energy (e.g., high voltage, sub-microsecond pulsing).

FIG. 3C shows another example of a pulse train that may be delivered by a system (e.g., high-voltage, fast pulsing electrical generator and catheter for delivery thereof). In particular, FIG. 3C shows an example of a voltage vs. time graph for sub-microsecond pulsing using a 15 kV peak for pulses 321 of 300 ns. The pulses may be repeated at a desired repetition rate 325, such as, e.g., between 0.1 Hz and 25 kHz or more. Thus, the apparatuses, including systems, described herein may include a pulse generator such as the one shown schematically in FIG. 1, configured to emit pulses in the sub-microsecond range, similar to the output parameters described above.

In general, these apparatuses may include a high-voltage connector for safely connecting the catheter device to a high-voltage power source. Examples of high-voltage connectors are provided below and described in detail in reference to FIGS. 14-19 below. As described above, these catheters are configured to apply high-voltage, fast pulsed electrical energy.

The high-voltage, fast pulsing catheters may be any appropriate length (e.g., between 6 inches and 100 inches, e.g., between 7 inches and 50 inches long, etc.) and may have any appropriate outer diameter, including, but not limited to between 1 French (F), e.g., ⅓ mm and 34 F (e.g., 11.333 mm) (between 3 F and 30 F, between 4 F and 15 F, 30 F or less, 25 F or less, 22 F or less, 20 F or less, 18 F or less, 16 F or less, 15 F or less, 14 F or less, 12 F or less, 10 F or less, 9 F or less, 8 F or less, etc.).

Any of these catheters may include one or more lumen, such as but not limited to one or more guidewire lumen, extending down the length of the device, including alone a midline (central lumen) or side lumen. These catheters may be compatible with any appropriate guidewire or guide catheter, including but not limited to a 0.035" guidewire.

Any of these catheters may be steerable. For example, in some variations the high-voltage, sub-microsecond catheters described herein may include one or more pull wires or tendons for steering any region of the catheter, including the distal tip, and/or more proximal regions. For example, in some variations, the catheters described herein may be configured to include one or more tendon for single-pull articulation. As will be described in greater detail below, the one or more tendons or pull wires may be configured to form part of an electrical pathway within the device.

The shaft of any of the catheters described herein may have a variable stiffness or a constant stiffness, or may include regions of varying or constant stiffness. In any of the catheters described herein the stiffness may generally be greater at the proximal end than the distal end. Alternatively or additionally, the distal end region (which may include the one or more electrodes, may be stiff or stiffenable (e.g., by the addition of a stiffening member, guidewire, etc.). Typically, the shaft of the device may be configured to be a torqueable shaft to provide a user with a full 360 degrees of selective rotation of the distal tip.

Any of the catheters described herein may be configured to include a force-applying member at the distal end region of the catheter (e.g., an inflatable balloon, hinged arm, expandable frame, etc.) for applying force to secure the one or more electrodes into the tissue and/or against the tissue. The force-applying member may be configured to drive the distal tip region including the electrodes against the tissue at or near the target tissue. As will be described in greater detail below, in some variations the electrodes and/or the distal end region of the catheter including the electrodes may be configured to penetrate into the tissue; in some variations the electrodes may be configured to controllably extend or project into the tissue when deployed by the user from the proximal end.

The one or more of the lumen of the apparatuses, including catheters, described herein may be used to apply or inject fluid, such as a conductive fluid. The application of a conductive fluid may be helpful to extend the applied field between the electrodes, or between the electrodes and the tissue being treated, when operating the apparatuses described herein. Conductive fluid may also or alternatively be used to transfer the field between the electrode and/or the tissue to improve the electrical contact between a target tissue and the apparatus. Any appropriate conductive fluid (and/or conductive gel) may be used. In some applications, for example, cardiac applications, one of the lumens of the catheter may be used to inject saline into a ventricle. In some variations one lumen or more may be used to deliver a visualization fluid (e.g., contrast agent, dye, etc.). In some variations, one lumen or more may be used for aspiration (e.g., vacuum). In some variations one lumen or more may be used for perfusing the tissue, including the target tissue.

The catheters described herein may be configured to reduce capacitive coupling that may otherwise arise from the electrical paths extending through the body of the catheter to the electrodes at the distal end. For example, any of these devices may include a coaxial conductor within the shaft to help reduce capacitive coupling effects. Non-coaxial conductors within the catheter shaft are also described herein.

Figure 4:
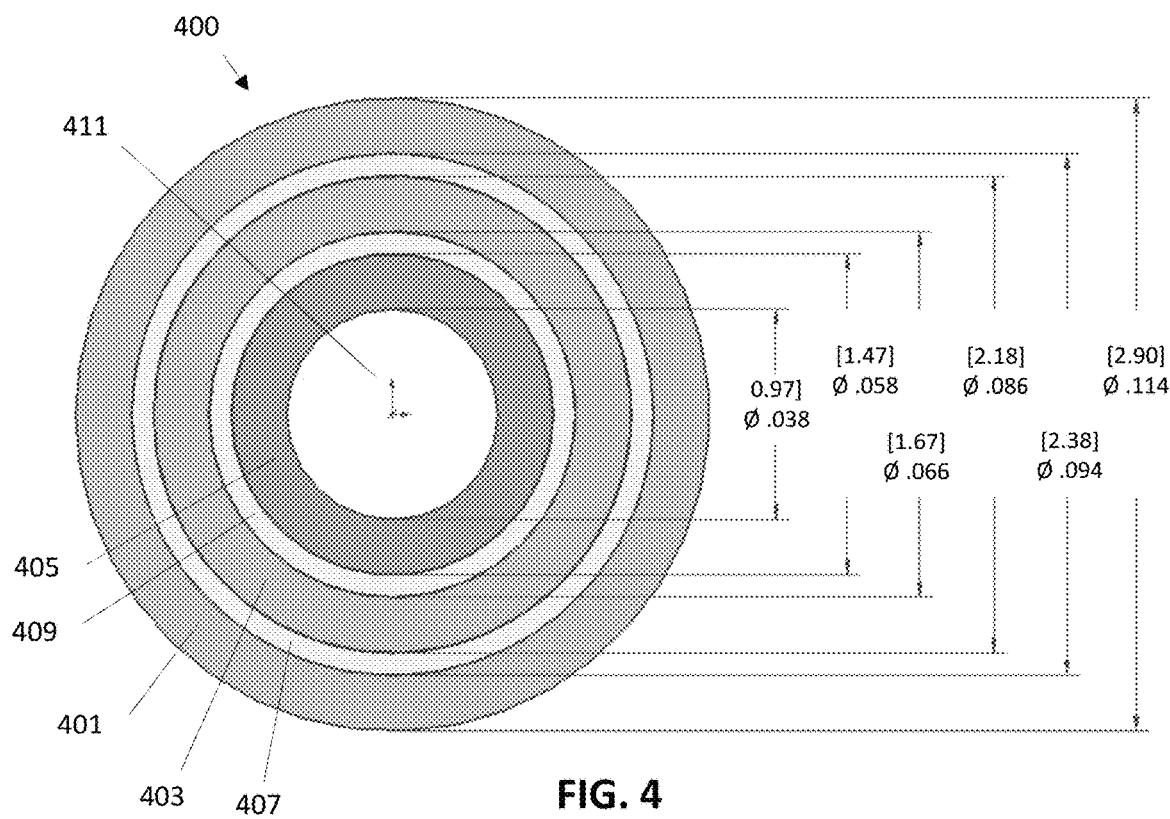
FIG. 4 is an example of a cross-section of a catheter configured for delivering high voltage, fast pulses of electrical energy.

For example, FIG. 4 illustrates one example of a cross-section of a flexible high-voltage, sub-microsecond catheter. In this example, the catheter includes five concentric layers, including three insulating (dielectric) layers 401, 403, 405 and two conductor layers 407, 409, comprising braided conductors. There is also a central inner lumen 411. The dimensions in millimeters (bracketed), shown on the right side of the figure, are for illustration only, and may be separately varied by, e.g., +/−1%, 5%, 10%, 15%, 25%, 50%, 75%, 100%, 150%, 200%, etc. or more.

In this example, the central inner lumen 411 is configured to be compatible with a standard (e.g., 0.035") guide wire. The Braid layers may be, e.g., braids of multiple 0.002" round SST 304V wire. Any appropriate braid pattern may be used, and the braid pattern may be adjusted along the length of the catheter to adjust the stiffness (including bending stiffness) of the catheter. For example, the braid may increase in braid angle of all or some of the number of filaments forming the braid (e.g. the angle of the braided material relative to the long axis of the catheter) towards the distal end of the catheter, reducing the relative stiffness of the catheter; the more parallel to the long axis the greater number of filaments are, the less stiff the catheter in this region may be. The braid pattern of the more inner layer 409 may be the same or different from the braid pattern of the more outer conductive layer 407. In some variations it may be beneficial to include braids having different braid angles in inner vs. outer layers.

The dielectric layers 401, 403, 405 may be, e.g., 0.010" Fluorinated ethylene propylene (FEP), having, e.g., a dielectric strength of about 2 kV/mil. Any appropriate insulating/dielectric material may be used. In the example shown in FIG. 4, the outer diameter of the shaft is approximately 3 mm; as mentioned the catheter may be larger or smaller.

In some variations, two or more additional layers (of, respectively, conductive material, including braided conductive material, and insulating/dielectric material) may be used (not shown). The thicknesses and orientation of these additional layers may be similar to that shown for the inner layers. In some variations the inner lumen may be partitioned, and/or may include one or more additional dedicated regions (e.g., imaging lines, fiber optics, etc.).

The electrodes for applying the high-voltage, fast (e.g., microsecond, sub-microsecond, nanosecond, picosecond, etc.) electrical energy may be configured to have any appropriate configuration, including, but not limited to, needle electrodes, surface electrodes, ring electrodes, band electrodes, disc electrodes, etc. For example, in some variations, the electrodes may have two or more 'bands' or rings around the distal end region of the catheter for delivery of the high-voltage, fast electrical energy. All or a portion of these rings or bands may be insulated to limit the application of energy to a particular face or region of the electrodes. The electrodes may be provided in pairs or a set (e.g., of two or more) for the delivery of energy. For example, an array of electrodes at the distal end may provide energy to the target tissue. In some variations the electrodes may be spaced apart from each other by a minimum distance. For example, the spacing between adjacent electrodes configured to apply high-voltage, fast electrical energy may be at least 0.2 mm, at least 0.3 mm, at least 0.4 mm, at least 0.5 mm, at least 0.6 mm, at least 0.7 mm, at least 0.8 mm, at least 0.9 mm, at least 1 mm, at least 1.2 mm, at least 1.3 mm, at least 1.5 mm, at least 1.7 mm, at least 2 mm, at least 2.2 mm, at least 2.5 mm, etc.

Figure 5:
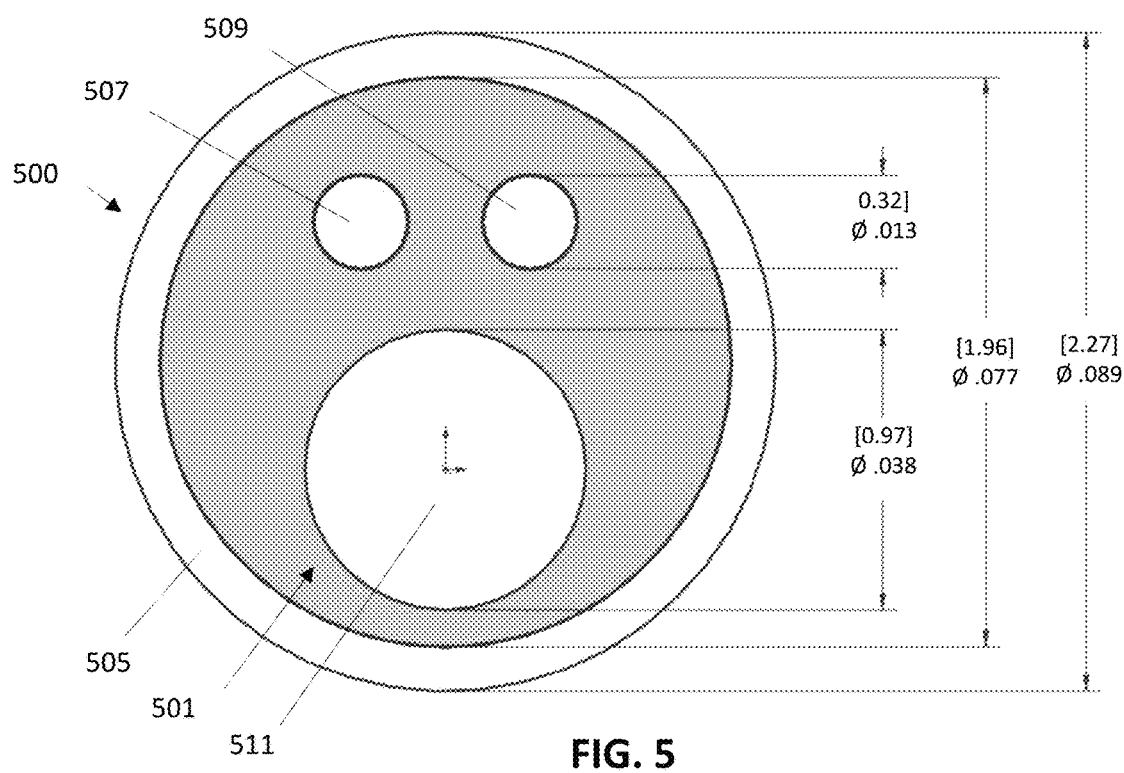
FIG. 5 is an example of a cross-section of a catheter configured for delivering high voltage, fast pulses of electrical energy.

FIG. 5 is an example of a transverse section of a flexible high-voltage, sub-microsecond non-concentric lumen catheter 500. In FIG. 5, at least a portion or a full length of the catheter may include a non-concentric arrangement of the dielectric insulator and two (or more) electrical lines, as shown. In this example, the conductive wires 507, 509 are separated from each other and from the inner lumen 511 (e.g., guidewire lumen) by a single, large dielectric/insulator 501. The outside of the catheter may include a braided jacket 505, which may be configured as to adjust/provide torsional stiffness of the catheter; this braided jacket may be a conductive material (similar to the conductive wires 507, 509), and set to ground and/or it may be non-conductive. It should be understood by those skilled in the art that the example of the non-concentric arrangement of FIG. 5 is just one possible configuration. In other examples, the conductive wires 507 and 509 may be located on either side of the lumen 511, or they could be combined and run down (e.g., as a twisted pair) a single/larger lumen (not shown). As in FIG. 4, the inner lumen 511 may be configured to accommodate a typical 0.035" guide wire. In this example, the dielectric distances may be, e.g., 0.010" of FEP, for example, and may be conductor-to-conductor, conductors-to-guidewire, and/or conductors-to-braided jacket. In FIG. 5, the outer shaft may be any appropriate dimension, including, e.g., 2.27 mm in outer diameter as shown; in some variations the outer diameter may be reduced if the braid is a non-conducting layer that may be included within the dielectric/insulator 501.

Figure 6:
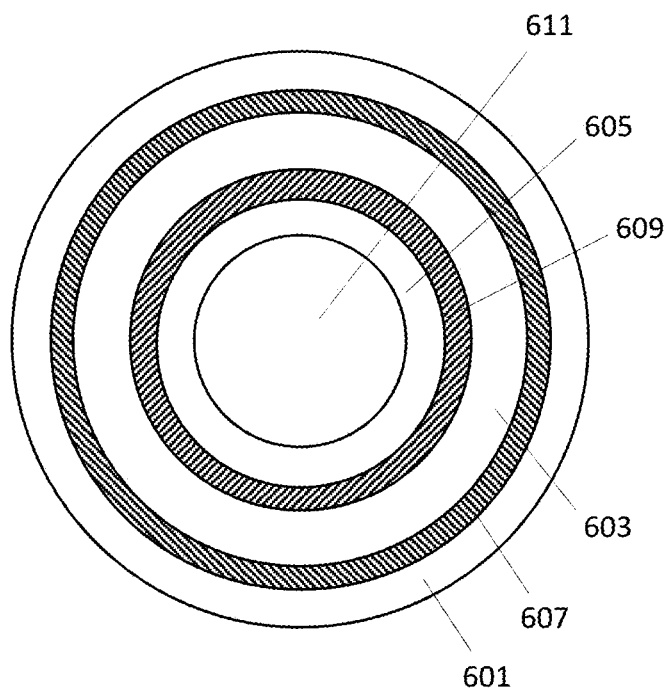
FIG. 6 is an example of a cross-section of a catheter configured for delivering high voltage, fast pulses of electrical energy.

FIG. 6 is another example of a transverse section of a high-voltage, sub-microsecond catheter. In this example, the catheter includes five concentric layers, including three insulating (dielectric) layers 601, 603, 605 and two conductor layers 607, 609. The insulating layer insulate to a minimum of 18 kV (e.g., using 9 or more mil FEP, 6 or more mil of Polyimide, etc.) of insulation around each conductive element. In this example, the inner guidewire channel 611 may have an ID of 0.038 inches, and an OD of 0.042 inches and be surrounded by the inner dielectric layer 605. The inner conductor layer 609 may be formed of a plurality of braided conductive filaments, as mentioned above. The middle dielectric layer 603 may be at least partially surrounded by the outer conductive layer 607, which may also be formed of a plurality of braided conductive filaments. In this example, the inner conductive layer has an OD of 0.050 inches, the middle insulation layer has an OD of 0.080", the outer conductive layer has an OD of 0.088 inches, and the outer insulating layer 601 has an OD of 0.118 inches. The outer diameter of the catheter is approximately 3 mm.

The electrodes at the distal end of the catheter may be configured to withstand, for example, 3 kV (dielectric strength) or more (e.g., at least 4 kV, at least 5 kV, at least 9 kV, at least 10 kV, at least 12 kV, at least 15 kV, at least 18 kV, at least 20 kV, at least 22 kV, at least 25 kV, at least 30 kV, etc.). In some variations, the electrodes are configured to withstand a minimum, e.g., for safe delivery of effective nano-pulse energy levels, of at least 1 kV (e.g., at least 5 kV, at least 9 kV, at least 10 kV, at least 12 kV, at least 15 kV, etc.).

In general the catheters described herein are also configured to withstand torque. For example, in some variations the conductors configured to carry the high-voltage, fast (e.g., sub-microsecond) pulsed electrical energy are woven/braided conductive layers. These woven layers may be, e.g., a metallic braid of conductive filaments, such as stainless steel (e.g., 304V SST), nickel-titanium (Nitinol wires), and/or other conductive filaments. The filaments and/or the braid pattern may be configured to increase or improve torquability. For example, the filaments may be flat (e.g., may have rectangular cross-sectional diameters of between 0.0001 and 0.002 on a short side and between about 0.0015 inches and 0.006 inches on a longer side, such as 0.0005"×0.0015", 0.001"×0.003", 0.002"×0.006", etc.). Alternatively, the filaments may be oval, round or rounded (e.g., diameter of between about 0.002 inches and 0.006 inches, etc.). In some variations the number of wire crosses per linear inch ("pic count") may be relatively high, providing a high density, typically low braid angle, or low, providing a lower density, low braid angle. As mentioned above, the braid angle (e.g., the pic count) may vary along the proximal-to-distal length to control flexibility, kink resistance and torsional stiffness. In some variations the braid pattern may be selected and/or modified (e.g., along the length of the catheter). Any appropriate braid pattern may be used, including a "regular" braid pattern (one over two wires, under two wires, etc.), "diamond" braid pattern (two over two wires, under two wires), "half-diamond" (one over one wire, under one wire, etc.), or the like. The braid pattern may be different along the length to provide variations in torsional stiffness and kink resistance.

In any of the catheters described herein a non-metallic material may be used for either or both the conductive layer and/or a non-conductive layer, that may modify/adjust the mechanical properties of the catheter. For example, any of these catheters may include a non-metallic braid material as a conductive layer and/or a sheath that is made of a Kevlar (e.g., stranded) material, a Polyethylene terephthalate (PET) material, liquid crystal polymer (LCP) monofilament, etc. Non-metallic materials may be MRI-compliant.

Figure 7A:
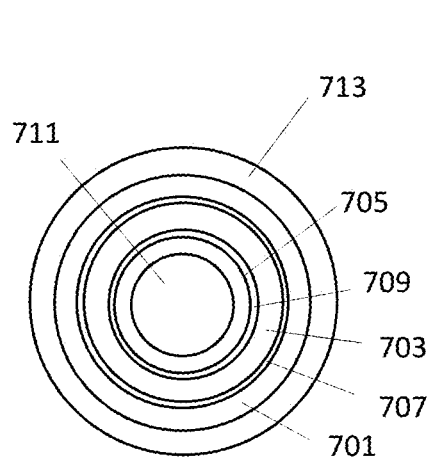
FIGS. 7A and 7B schematically show cross-sections of examples of catheters with outer insulating jackets.
Figure 7B:
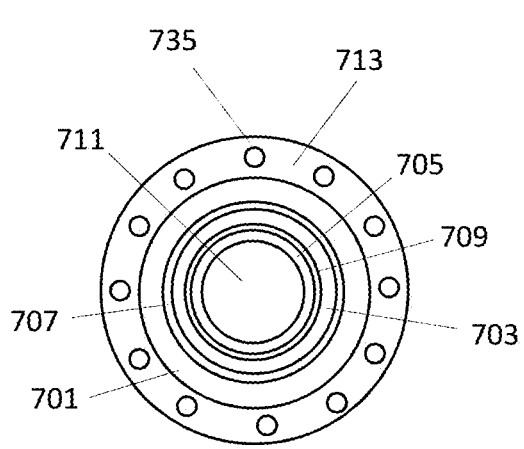

Any of the catheter devices described herein may include a jacket layer (e.g., an outer jacket), as mentioned above. For example, FIGS. 7A and 7B illustrate examples of cross-sections through catheters including an outer jacket 713 surrounding the rest of the catheter. These catheters are shown having a configuration similar to that shown in FIGS. 4 and 6, described above, although other configurations (including the non-concentric configurations such as shown in FIG. 5) may be used. In FIGS. 7A and 7B, the catheter includes a central lumen 711, three insulating/dielectric layers 701, 703, 705 and two conductive layers 707, 709. The outer jacket 713 may be present along all or a portion (e.g., proximal portion) of the catheter; in some variations the jacket may modify the flexibility of the catheter so that it is relatively stiffer more proximal and relatively more flexible more distally. The jacket may be formed of any appropriate material, including, but not limited to thermoplastics (e.g., PU, Nylon, Pebax, etc.), thermoset materials (e.g., Silicone, PI, etc.). The jacket may have an outer diameter that is constant or may vary along the length. For example, the outer diameter may vary from 3 F-30 F. In some variations the catheter may be made lubricious by including a lubricious material or outer coating (e.g., as part of or applied to the outer surface, including the jacket). The material forming the outer jacket may adjust the durometer (e.g., harness). In any of these variations the outer jacket may be formed of a material that resists physical damage (e.g., puncture, crushing, etc.), which may otherwise interfere with the electrical isolation of the conductive elements of the catheter.

The outer jacket for the catheter may include a braided or coiled material. The braided or coils (e.g., one or more helically wound elements arranged around the circumference of the catheter) may be used to provide structural support and/or otherwise modify the physical properties of the catheter. In some variations the outer jacket region may include one or more channels for pull wires (e.g., tendons), fiber optics (for visualization, illumination, treatment, sensors, etc.), and/or for additional electrical conductors (e.g., low voltage/low current connectors, e.g., for one or more sensors, etc.). For example, FIG. 7B shows an example of a catheter including an outer jacket 713 that is surrounded by a plurality of channels 735. These channels may include (and/or be filled with) one or more pull wires, optical fibers, vacuum lines, injection ports for conductive fluid, etc. as mentioned. When pull wires are used, the pull wire may be any appropriate material (e.g., stainless steel, stranded cable, stranded polymer, e.g., Dyneema, etc.). A pull wire may extend down the entire length of the catheter (to the distal end) or it may terminal before the distal end of the catheter to provide bending in particular location. Multiple pull wires may be arranged in positions around the perimeter of the catheter either symmetrically or asymmetrically. The central lumen 711 in both FIGS. 7A and 7B may also be used to pass one or more elements, including, but not limited to, a guidewire. Either or both the inner walls of the central lumen and/or peripheral channels may be lined or coated with a material, such as a polymeric material, lubricious material, etc., including a Teflon material. In some variations the outer jacket is the same as the outer insulator/dielectric layer 701.

Any of these catheters may include a stacked coil tube configured to prevent compression of the shaft during articulation.

Conductors, including the conductive layers, for conducting the high-voltage, fast pulse (e.g., sub-microsecond) energy may be stranded conductors, as described above, however in some variations the conductors may also include one or more solid cores, which may be larger-diameter strands, etc.

Any of the catheters described herein may be configured to articulate, e.g., by pulling and/or pushing one or more tendons, by inserting a curved or bendable steering element through a lumen, etc. In some variations the catheter includes a jacket or other layers (including the conductive layers) with different materials, different durometers, etc. to vary the stiffness and the provide regions for localized articulation, including articulation of specific segments of the shaft (e.g., the distal tip region).

FIGS. 8A-8D illustrate example of catheters having one or more pull wires. For example, in FIG. 8A, a cross-section of a catheter showing a pull wire 838 on the top. The catheter includes two non-concentric conductors 807, 809, and a central channel 811 (e.g., for a guidewire) as well as a surrounding insulator/dielectric material 803. An additional outer jacket 813 may also be included. In variations having a single pull wire 838, the device may be biased to return to a shape (e.g., linear shape, curved shape, etc.) so that releasing tension on the pull wire allows the catheter to resume a pre-set shape. FIG. 8B shows a similar catheter with a pair of pull wires 838, 838' on opposite sides of the catheter. In some variations, a catheter may include three (e.g., separated by 120 degrees) or more (four, five, six, etc.) pull wires. FIGS. 8C and 8D show similar examples with concentric conductive layers 807, 809 and insulating/dielectric layers 801, 803, 805, surrounding the central opening 811.

FIGS. 9A-9C illustrate bending of a high-voltage, sub-microsecond pulsing catheter as described herein. In FIG. 9A, a cross-sectional view of the catheter 900 is shown, showing two conductive layers 907, 909 concentrically arranged along the length of the catheter and each connecting to an electrode 917, 919 on the outer lateral surface of the catheter. The insulating layers 901, 903, 905 may surround the conductive layers and may be sufficiently thick and have dielectric properties allowing them to insulate, depending on particular requirements or application, for example to greater than 1 kV (e.g., 2 kV or more, 3 kV or more, 5 kV or more, 8 kV or more, 9 kV or more, 10 kV or more, 12 kV or more, 15 kV or more, etc.). FIG. 9B shows a cross-section of the catheter through line B in FIG. 9A. Two tendons 938 and 938' (pull wires) may be used to articulate the catheter, as shown in FIG. 9C, showing bending in two directions. This bending may be used to help navigate the catheter and may also be used to help drive the catheter against a target tissue, as described in more detail below.

The catheters described herein may have an increase pushability/trackability to provide column strength when bending/advancing the catheter. Catheters with more flexible distal ends may have improved performance when, e.g., crossing tortuous anatomy to reach a target treatment region. In some variations all or a portion of the length of the catheter may be configured to have a braided construction (as described above) modifying the flexibility, one or more coils or coil tubes (including stacked coils) to modify the flexibility, one or more cut hypotubes (e.g., to vary the flexibility, torque properties, etc.) or the like.

The catheters devices described herein may be used with one or more accessory devices, including, but not limited to guidewires of any appropriate size (e.g., 0.14 inch diameter, 0.018 inch diameter, 0.035 inch diameter, etc.) or material (nickel titanium, stainless steel, polymer, etc.), including steerable guidewires. These catheters may also be used with an introducer sheath (e.g., 4F-12F, sized by internal diameter, or other appropriate sizes), a transseptal sheath, a trocar (e.g., 3, 5, 10 mm trocar), and may be used with or form part of an endoscope (e.g., colonoscope, bronchoscope, gastroscope, etc.).

Figure 10A:
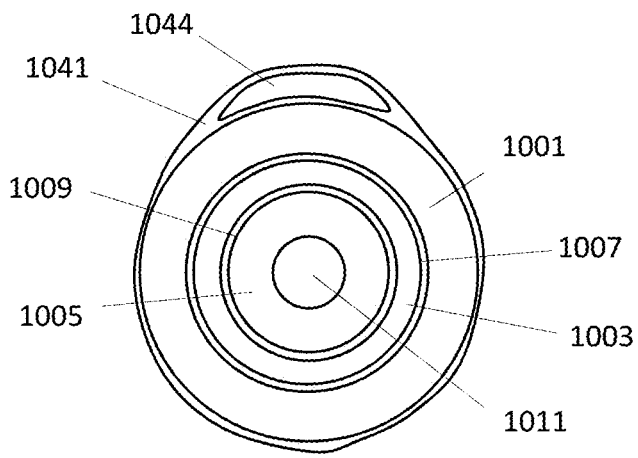
FIG. 10A shows an example of a cross-section of the distal end of a catheter configured for the delivery of high-voltage, fast pulsed electrical energy including an inflatable tip biasing element.
Figure 10B:
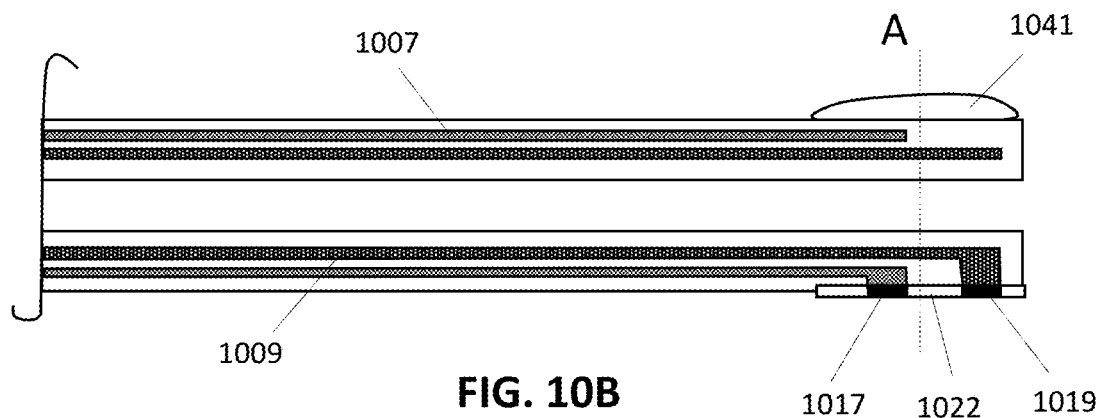
FIG. 10B shows the catheter of FIG. 10A with the inflatable tip-biasing element un-inflated.
Figure 10C:
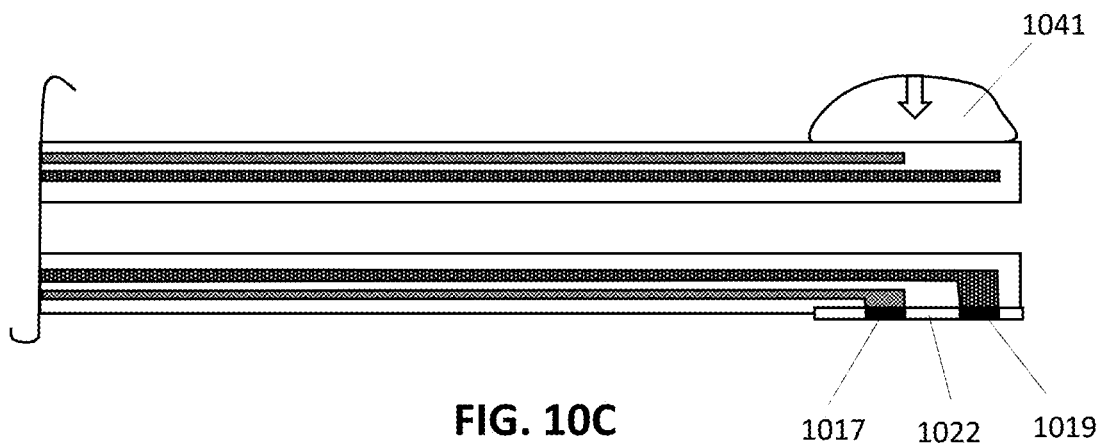
FIG. 10C shows the catheter of FIG. 10A with the inflatable tip-basing element inflated.

Any of the catheters described herein may include a bias that may be actuated to drive the electrode(s) against the target tissue and/or into the tissue to reach the target tissue. FIG. 10A-10C illustrates one example of a catheter configured to deliver high-voltage, fast pulse (e.g., sub-microsecond) energy to a target tissue. In FIG. 10A a cross section through the catheter shows a central lumen 1011 concentrically surrounded by three insulating layers 1001, 1003, 1005 themselves surrounding two conductive layers 1007, 1009. An outer inflatable balloon 1041, having an inflatable lumen 1044 at least partially surrounds the catheter (e.g., a distal tip region of the catheter). This balloon may be inflated to drive the electrodes (not visible in FIG. 10A) against the tissue, as shown in FIGS. 10B-10C. In FIG. 10B the balloon 1041 is deflated, while in FIG. 10C the balloon may be inflated (e.g., by saline) and may push against a vessel wall (not shown) to drive the electrodes 1017, 1019 against the target tissue. The electrodes may be separated by an electrically insulating material 1022 to a minimum separation distance (e.g., 0.5 mm, 1 mm, 3 mm, 4 mm, 5 mm, 6 mm, etc.). In some variations the balloon material may be electrically insulating. The balloons may be formed of a low-compliance material (e.g., Pebax, Nylon, PET, etc.) or a high-compliance material (e.g., PU, silicone, TPEs such as chronoprene, polyblend, etc.), and may have burst pressures of greater than 30 atm. In some variations (not shown in FIG. 10A-10C) the electrodes may be on the balloon outer surface.

Figure 11:
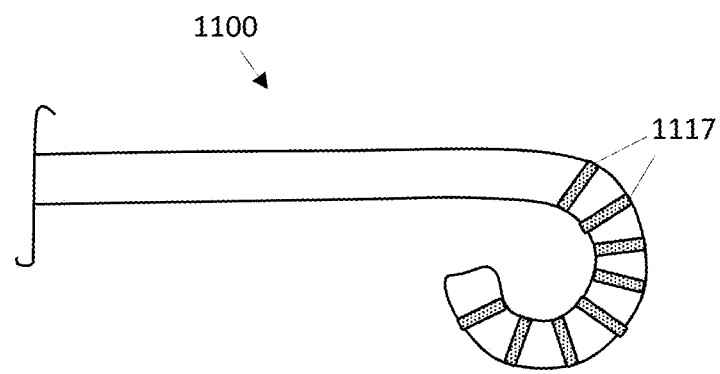
FIG. 11 is an example of a catheter configured for the delivery of high-voltage, fast pulses for use in an atrial ablation.

The catheter may be configured for ablation, including ablating tissue such as cardiac (e.g., left atrial ablation) tissues, lung tissue esophageal, gastric, etc., including tumors. For example, the apparatuses described herein may be used to treat, e.g., the bronchial passages to reduce mucus to treat COPD or bronchitis, emphysema, etc. FIG. 11 illustrates one example of a catheter device configured for ablating cardiac tissue, including a plurality of band electrodes 1117 along the outer length of the catheter 1100. The distal end of the shaft may be highly flexible, as shown.

Figure 12A:
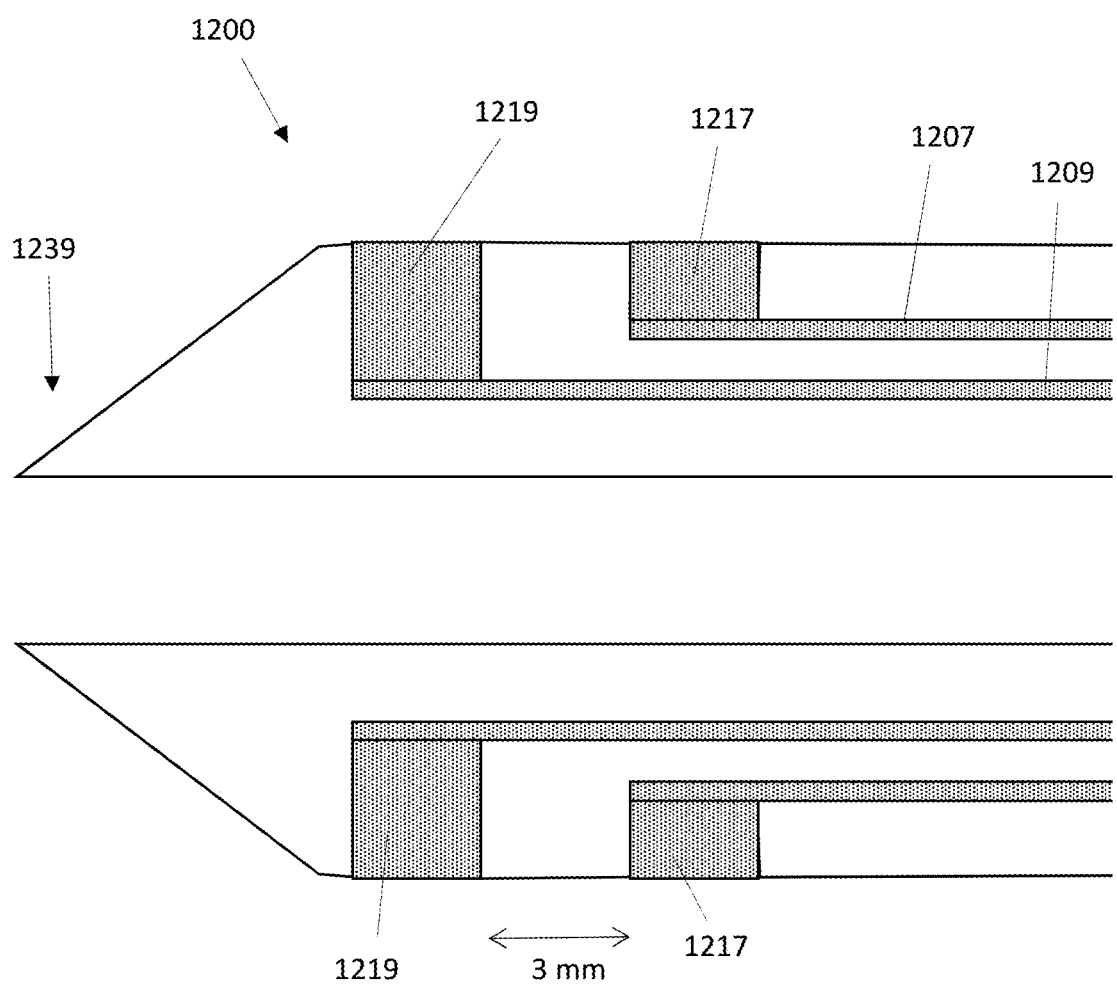
FIGS. 12A-12C are examples of a distal tip region, including electrodes of a catheter configured for the delivery of high-voltage, fast pulses.

In general, the one or more electrodes may be positioned on the distal tip of the catheter and may be configured to prevent make electrical contact with the target tissue, while avoiding electrical contact with non-tissue, electrical interference and/or arcing. One or more electrodes may be connected to the conductive layers. For example, FIG. 12A shows one example of a catheter 1200 having a pair of ring electrodes 1217, 1219 each connected to conductive layer 1207, 1209. The catheter has a tissue-penetrating distal tip 1239, and may be used, e.g., to penetrating a tissue such as a tumor, to apply treatment.

Figure 12B:
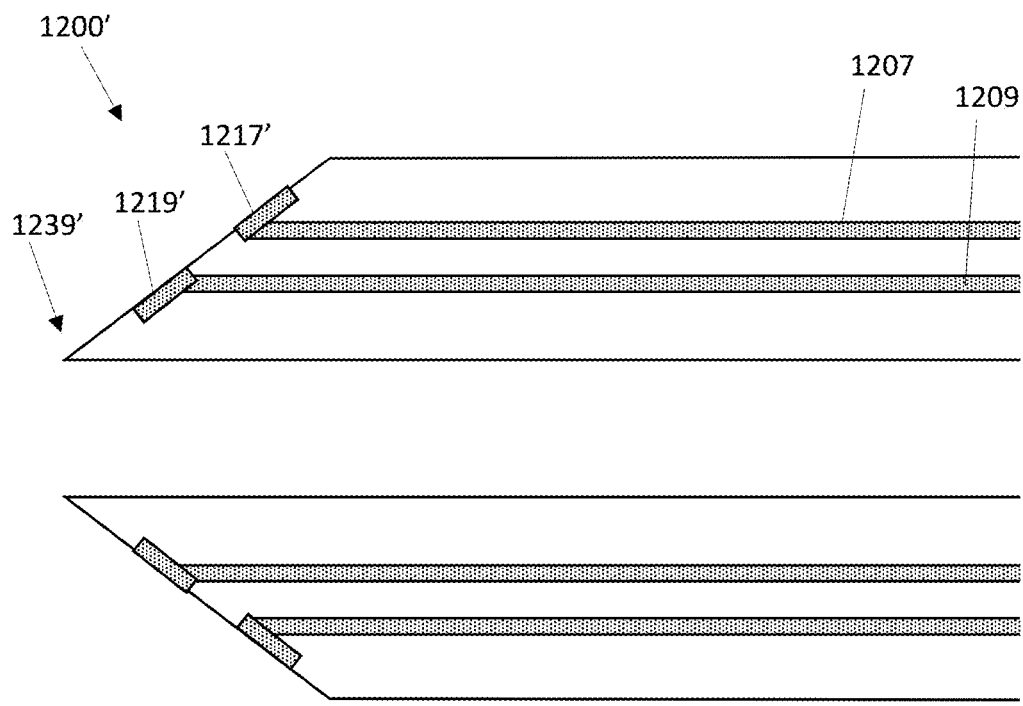
Figure 12C:
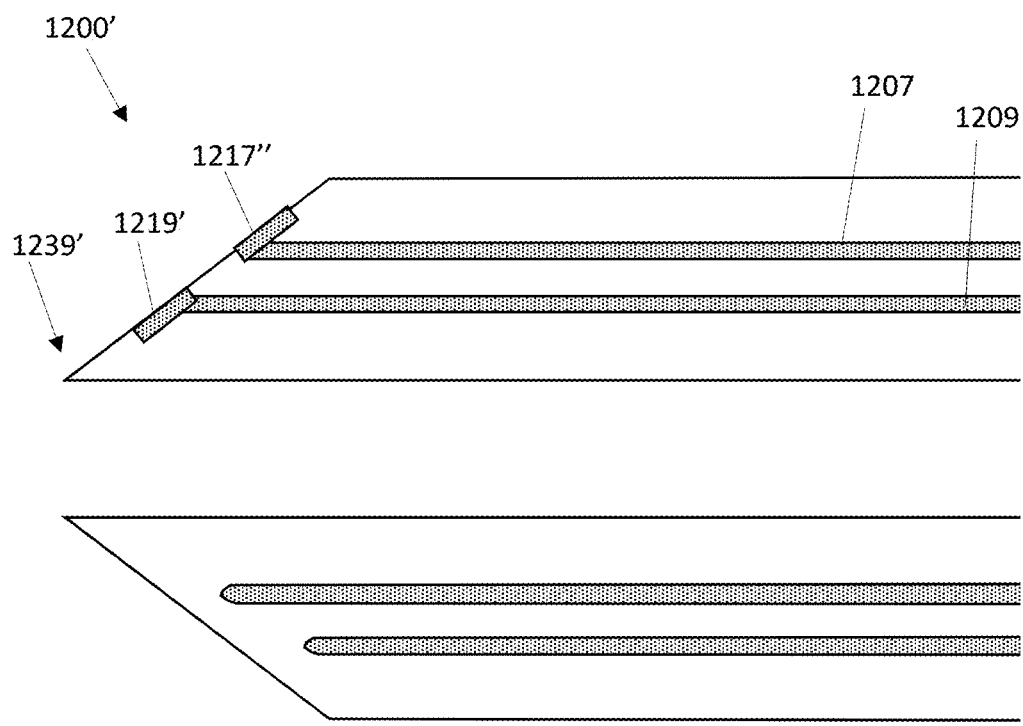

Although the majority of the catheters described herein include one or more sets of electrode pairs on the lateral side of the catheter, typically at or near the distal tip, in some variations one or more electrodes may be positioned facing distally from the distal tip of the electrode. For example, FIGS. 12B and 12C illustrate examples of catheters having electrodes at the distal tip that face distally. In FIG. 12B, the distal-facing electrodes 1217, 1219 are connected as ring electrodes on the tissue-penetrating distal end of the catheter; in some variations at least a portion of this distal facing ring may be insulated, reducing the size of the distal-facing electrodes. In FIG. 12C, for example, smaller distal-facing electrodes 1217", 1219" are exposed. FIGS. 12A-12C shows examples of catheters having pointed (e.g., tissue-penetrating) distal tips that may be used, for example, with a guide wire that may penetrate the tissue, such as a tumor. The distal-facing electrodes may also be used with non-tissue penetrating tips. In addition, the electrodes themselves may be tissue-penetrating, and may be configured to extend from the catheter into the tissue when deployed.

Figure 13:
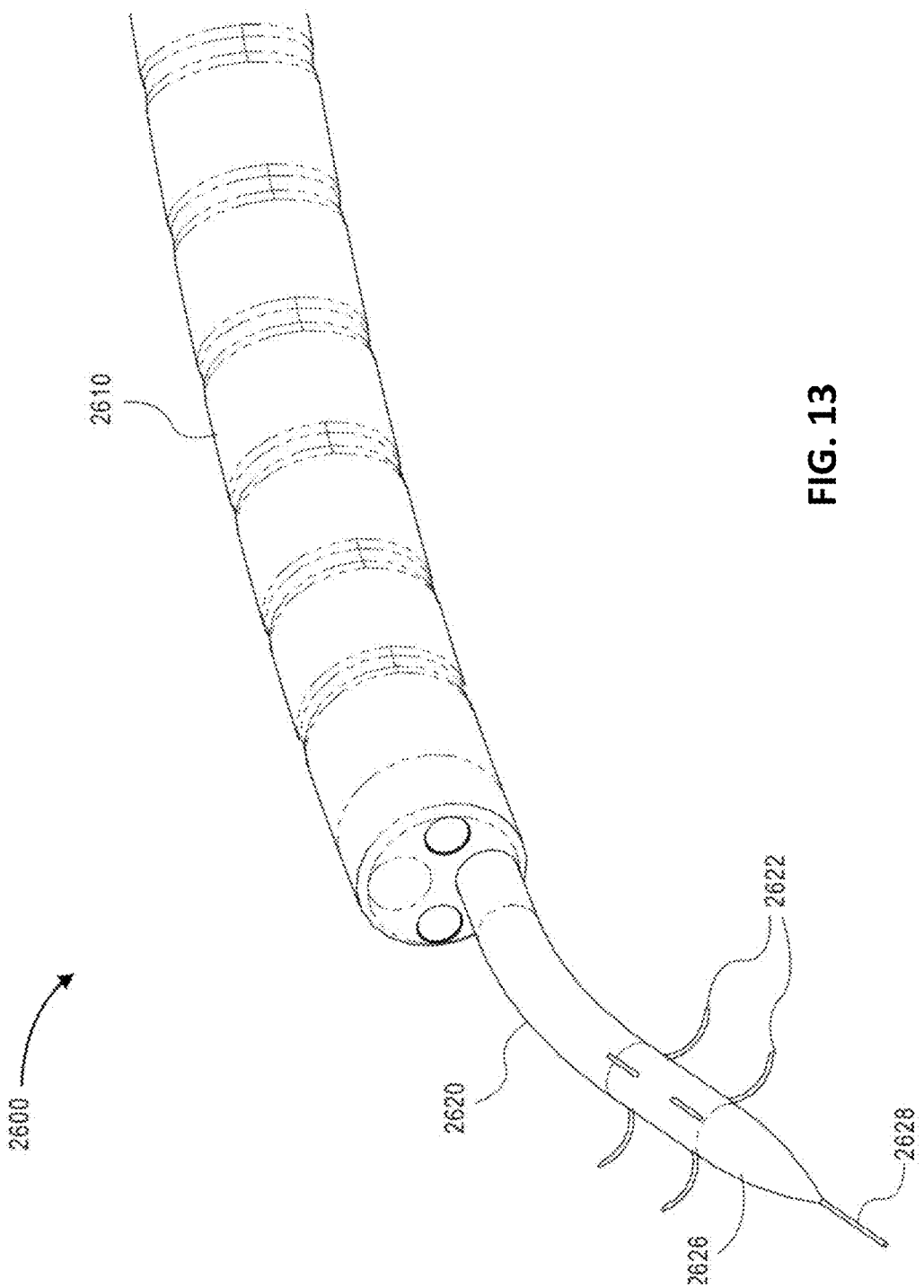
FIG. 13 shows yet another example of a catheter instrument which may be used to deliver high-voltage, fast pulses of electrical energy.

FIG. 13 shows an example of a system 2600 including a catheter 2620 that may be used to deliver high-voltage, fast pulse energy to a target tissue, for example to contact a patent with terminals percutaneously or endoluminally during treatment. In this example, the catheter 2620 includes tissue-penetrating electrodes 2622 that extend from the distal end region of the catheter which itself extends from an endoscope 2610. For example, catheter 2620 may be routed through a lumen in the endoscope 2610. The catheter 2620 includes electrically insulating portions 2626 and positive and negative electrically conductive electrodes 2622. In some embodiments, catheter 2620 also includes or allows passage of a guide wire (or flexible needle) 2628 to help penetrate through tissue. Any of the catheters described herein may include a thermocouple thermally connected to either of its terminals.

Although many of the examples illustrated above show only two conductive layers, in some variations, multiple conductors (e.g., conductive layers) may be included, and may allow multiple different sets of electrodes to be separately actuated. For example, additional conductive layers may be concentrically arranged. In some variations the conductive layer may be divided up into helically arranged (and separate) conductive regions for separately actuating electrodes.

The catheters described herein, and particularly the configuration of the conductive and insulating portions may be configured to prevent electromagnetic interference (EMI) even at the high voltages and rapid pulse rates (e.g., sub-microsecond pulsing) used herein. In particular, EMI may be problematic for electronics on or adjacent to the catheter, including robotic delivery systems, sensors, and the like. For rapid pulsing, including nanosecond and sub-nanosecond pulsing, it may be undesirable to widely separate the leads (e.g., positive and negative leads), as this may result in EMI issues in some configurations, including poorly controlled or incorrect impedance. Thus, in some variations of the catheters described herein, the conductive leads (e.g., conductive layers) may be arranged to reduce electrical loop area, to prevent radiation of energy (e.g. in which the lead may act as an antenna). Traditional conductive wires may be twisted together (forming a twisted pair) so that any field that is generated by the space between the conductive lead changes polarity as it extends along the length, and at a reasonable distance from the conductive lead the field is more effectively cancelled. However, the faster the pulsing, the greater the number of twists/inch that may be needed to effectively reduce emitted radiation; further, twisting the cables in this manner may require a large wall thickness. Thus, in some variations, the catheters described herein may use positive and negative leads in a coaxial configuration, as shown above. In some variations the catheters are configured to have a coaxial impedance that remains relatively high; even with smaller electrodes, the impedance between the catheter electrodes may be within the 200-ohm range.

For example, two coaxial braids may be used, one for the positive lead and the second for the negative lead. This may minimize EMI during the high-powered rapid (e.g., nanosecond) pulsing. Further, the impedance may be better controlled, enabling more reliable pulse and power delivery to the electrodes. As mentioned above, this configuration may be used with one or more additional wires extending in the conductive layer (e.g., within the braid, which may also have structural significance to the catheter's mechanical properties) without negatively impacting the control of impedance and the reduction in EMI.

In some variations, the conductive layer may be formed of a braid of conductive fibers that are also braided with an insulator (e.g., carbon fiber) and a good conductor to adjust the impedance. The cable characteristic impedance is typically the square root of the inductance/unit length (L) along the conductors divided by the capacitance/unit length (C) between the conductors. For two (or more) coaxial braids, as opposed to a coaxial cable, the L is smaller due to the wide conductors and the C is larger due to the increased surface area between the conductors. So, the braid impedance may be quite low, e.g., in the 20-ohm range. This potentially very low characteristic impedance can be increased by using very thin braid material, increasing L or using a conductive material for some of the braid strands, which can increase C. For example, a braid may be configured to achieve characteristic impedances from 20-ohms to 150-ohms. For lower pulse voltage requirements (e.g., less than 5 kV, likely ≤2.5 kV) and potentially lower currents, a partially-conductive but uniformly distributed braiding (with insulating braid material making up much of the weave) could achieve ~150 to 200-ohm impedance and still have low enough resistance and good dispersion properties (dispersion is pulse width distortion cause by the higher-frequency pulse spectrum components attenuating more and propagating slower, phase shifting differently, than the lower-frequency components).

In any of these variations the catheter may include a high-voltage connection to the catheter. In some variations the catheter may include a high-voltage connector on the attachment to the pulse generator and/or a hand piece. In some variations, the device may include multiple (e.g., 2, 3, 4, 5, 6, etc.) connections at the interface with the pulse generator and/or hand piece. These connectors as well as the catheters may therefore meet minimum electrical insulation requirements and standoff of the high voltages from the fast pulsing (e.g. sub-microsecond, nanosecond, picosecond, etc. pulsing).

Connectors

FIGS. 14A and 14B are illustrations of one example of a high-voltage connector 2700 configured to be mated with a pulse generator (e.g., a housing cutaway portion 2750 of a pulse generator), as shown in FIG. 1. Connector 2700 may, for example, be used in system 100 to connect catheter 102 to housing 105. When mated, connector 2700 electrically connects the catheter 102 with the electronic components internal to housing 105, such as a pulse generator configured to deliver high-voltage, very fast (e.g., sub-microsecond) pulses. FIG. 14A illustrates connector 2700 and cutaway portion 2750 in an unmated position. FIG. 14B illustrates connector 2700 and cutaway portion 2750 in a mated position.

Connector 2700 may include a hole 2702 configured to receive a cable electrically contacting a catheter. Connector 2700 also includes a handle 2706 which includes internal conductors which electrically connect terminals 2704 with the cable. Handle 2706 can also include an insulating safety structure, such as a standoff skirt 2708, which is configured to provide at least a minimum clearance distance $d_{min\_user}$ along a surface of connector 2700 between a user's hand holding the connector 2700 by the handle 2706 (e.g., by a hand-grip portion of the handle in those applications where the device is hand-held) and terminals 2704 without increasing the total length of the connector 2700 or the actual physical distance between the terminals 2704 and a location on the handle of the connector where the user may place his or her hands or fingers.

A "minimum clearance distance from the user's hands" ($d_{min\_user}$) as used herein may include a shortest distance that avoids an arc in both the air and along an insulative material surface path to a grip portion for a user's hand. In other words, $d_{min\_user}$ includes a distance that is a greater of the following two distances: 1) a shortest distance or path that prevents an arc between two conductive parts measured along any surface or combination of surfaces of an insulating material, and 2) a shortest path in air between two conductive parts that prevents an arc. Addition of a standoff skirt, like the skirt 2708, also allows one to reduce the total length of the connector while providing a desired $d_{min\_user}$.

In some embodiments, the minimum clearance distance is equal to or greater than 0.5, 0.85, 1.0, 1.27, 2.5, 3.2, 3.8, 4.4, 5.1, 6.4, 7.6, 10.2, 12.7, or more centimeters (i.e., 0.20, 0.33, 0.39, 0.5, 1, 1.25, 1.5, 1.75, 2, 2.5, 3, 4, 5, or more inches).

As shown, terminals 2704 may be spaced apart from handle 2706 by spacers 2710, for example, by a distance greater than 1 inch. As shown, housing cutaway portion 2750 may include terminal receptacle holes 2752, which are configured to receive terminals 2704 of connector 2700 when connector 2700 is mated with housing cutaway portion 2750. In this embodiment, housing cutaway portion 2750 also includes one or more skirt receptacle holes 2754, which is configured to receive standoff skirt 2708 of connector 2700 when connector 2700 is mated with housing cutaway portion 2750.

To increase the distance of a shortest path along the surface of connector 2700 between electrically conductive terminals 2704 and the user's hand, in this embodiment, standoff skirt 2708 includes two concentric ring portions. The concentric ring portions surround both spacers 2710 and may be centered between the two spacers 2710. In addition, housing cutaway portion 2750 includes two skirt receptacle holes 2754. In alternative embodiments, a connector has just one or more than two concentric ring portions and a corresponding housing cutaway portion has just one or more than two skirt receptacle holes.

Figure 15A:
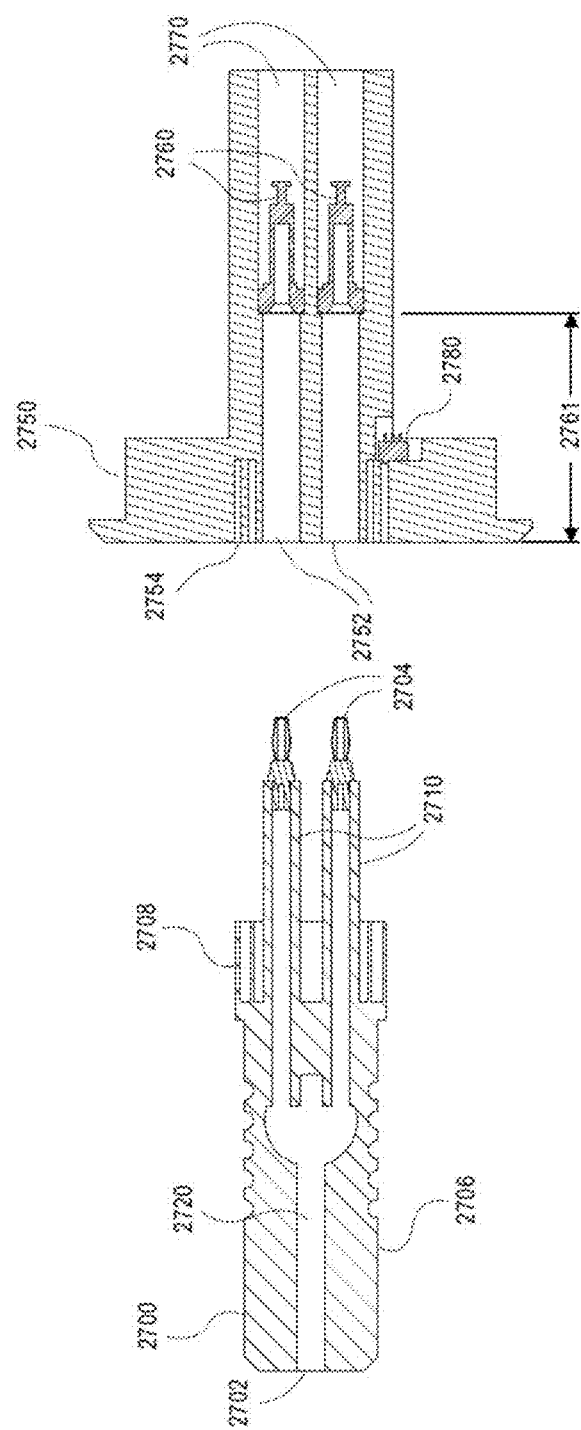
FIG. 15A shows a cross-sectional view of an example of a high-voltage connector and a portion of a housing of a pulse generator (shown as a cutaway portion).
Figure 15B:
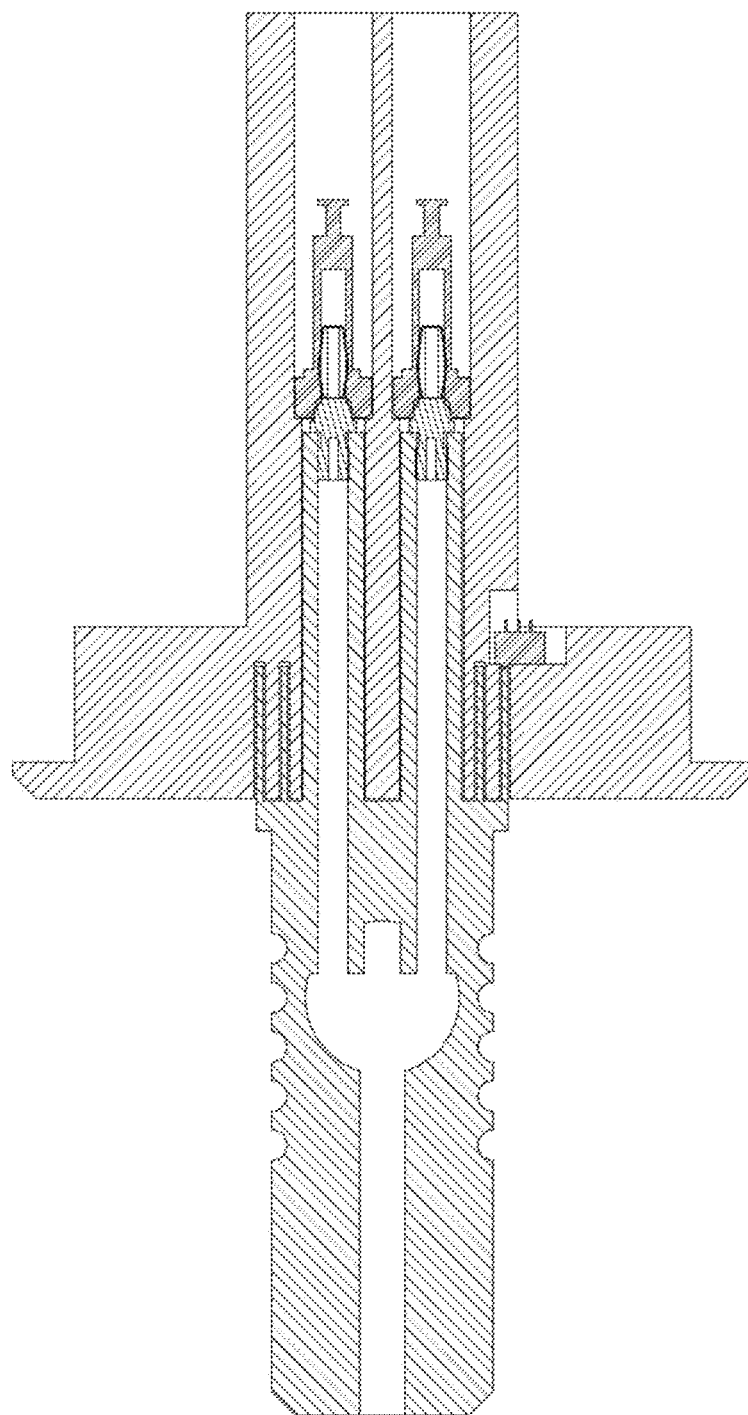
FIG. 15B shows a cross-section of a high-voltage connector and a housing cutaway portion with the connector engaged.
Figure 15C:
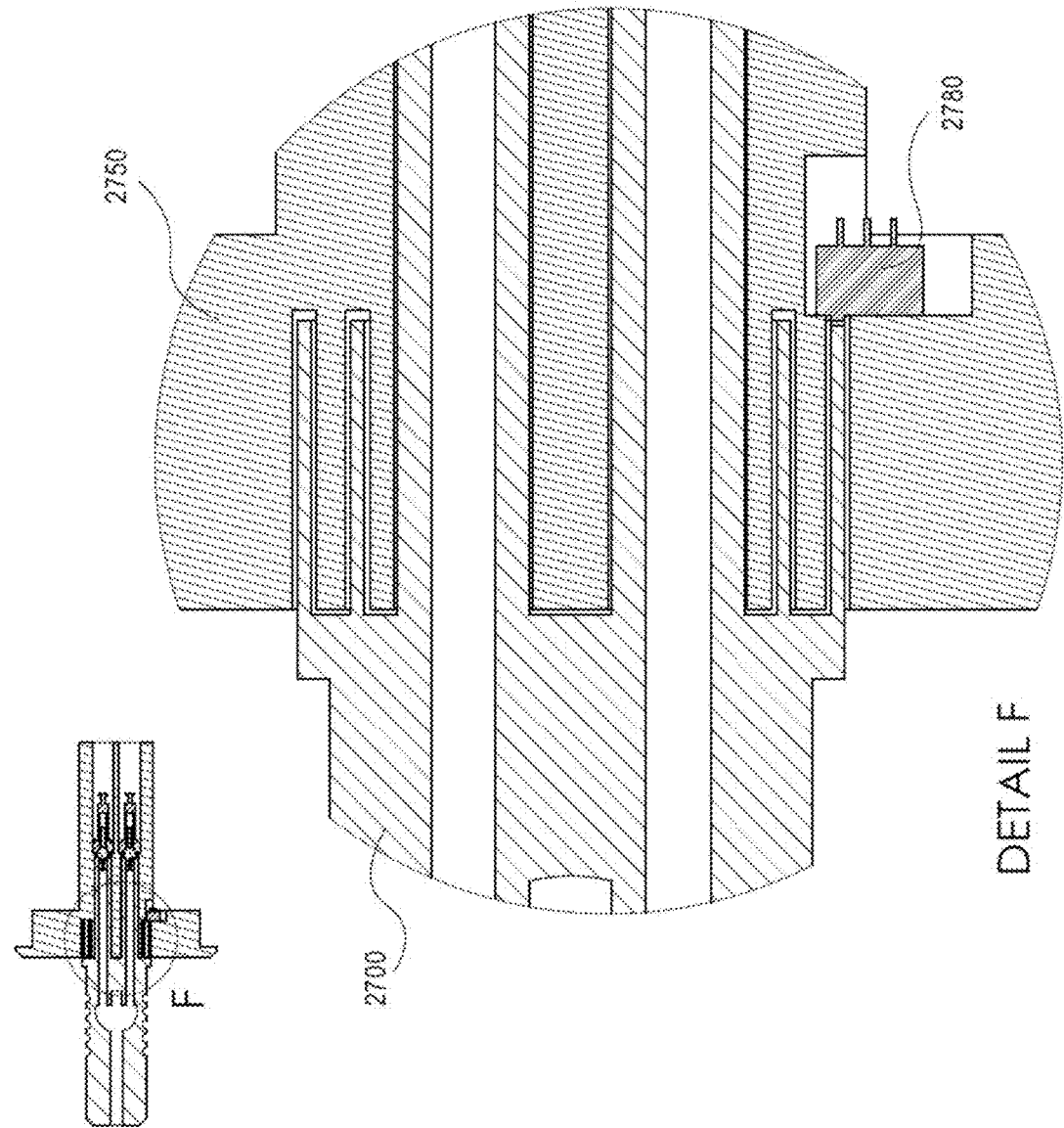
FIG. 15C shows an enlarged higher-detailed view of the engagement of a high-voltage connector.

FIGS. 15A, 15B, 15C, and 15D are illustrations of a cross-sectional view of connector 2700 and housing cutaway portion 2750. The plane of the cross-sectional view is defined by the axis of the terminal receptacle holes 2752 illustrated in FIG. 14A. FIG. 15A illustrates connector 2700 and cutaway portion 2750 in an unmated position. FIGS. 15B and 15C illustrate connector 2700 and cutaway portion 2750 in a mated position, where FIG. 15C illustrates in detail F an enlarged view of portions of connector 2700 and cutaway portion 2750. The connector may be integrated into any of the catheters described herein, at a proximal end and/or following a handle also coupled to the catheter.

As shown in FIG. 15A, connector 2700 includes cavity 2720 configured to include wiring (not shown) which electrically connects the cable with terminals 2704. Cavity 2720 may also include wiring to connect to one or more thermocouples connected to one or more of the terminals of the catheter.

Housing cutaway portion 2750 may include female terminals 2760 (FIG. 15A) which are configured to receive male terminals 2704 when connector 2700 and housing cutaway portion 2750 are in the mated position. Setback distance 2761 is from a face of the housing cutaway portion 2750 to terminals 2760.

Housing cutaway portion 2750 may also include cavities 2770 which are configured to include wiring (not shown) which electrically connects terminals 2760 with the electronic components internal to the housing. As a result, when in the mated position, the electronic components internal to the housing are electrically connected with a therapeutic catheter via terminals 2760, terminals 2704, wiring between terminals 2704 and a cable, and the cable, which is electrically connected to the therapeutic catheter.

Housing cutaway portion 2750 also illustrates electromechanical switch 2780. As a result of connector 2700 and housing cutaway portion 2750 being in the mated position, electromechanical switch 2780 assumes a conductive state indicating that the connector 2700 and the housing cutaway portion 2750 are mated. In addition, as a result of connector 2700 and housing cutaway portion 2750 being in an unmaintained position, electromechanical switch 2780 assumes a conductive state indicating that the connector 2700 and the housing cutaway portion 2750 are unmated. Electromechanical switch 2780 may be connected to a controller (not shown) which may be configured to prevent electronic components internal to the housing from applying electrical signals to terminals 2760 as a result of connector 2700 and housing cutaway portion 2750 being unmated, or may be configured to allow electronic components internal to the housing to apply electrical signals to terminals 2760 as a result of connector 2700 and housing cutaway portion 2750 being mated.

In some embodiments, electromechanical switch 2780 includes circuitry configured to interface with the controller. For example, the controller may identify the connector 2700 or a catheter connected to the connector 2700 as a result of the controller receiving identifying information from the circuitry. In some embodiments, the circuitry may be configured to count and store the number of high-voltage, fast pulsing (e.g., sub-microsecond pulsing) pulses delivered through the connector 2700.

Figure 15D:
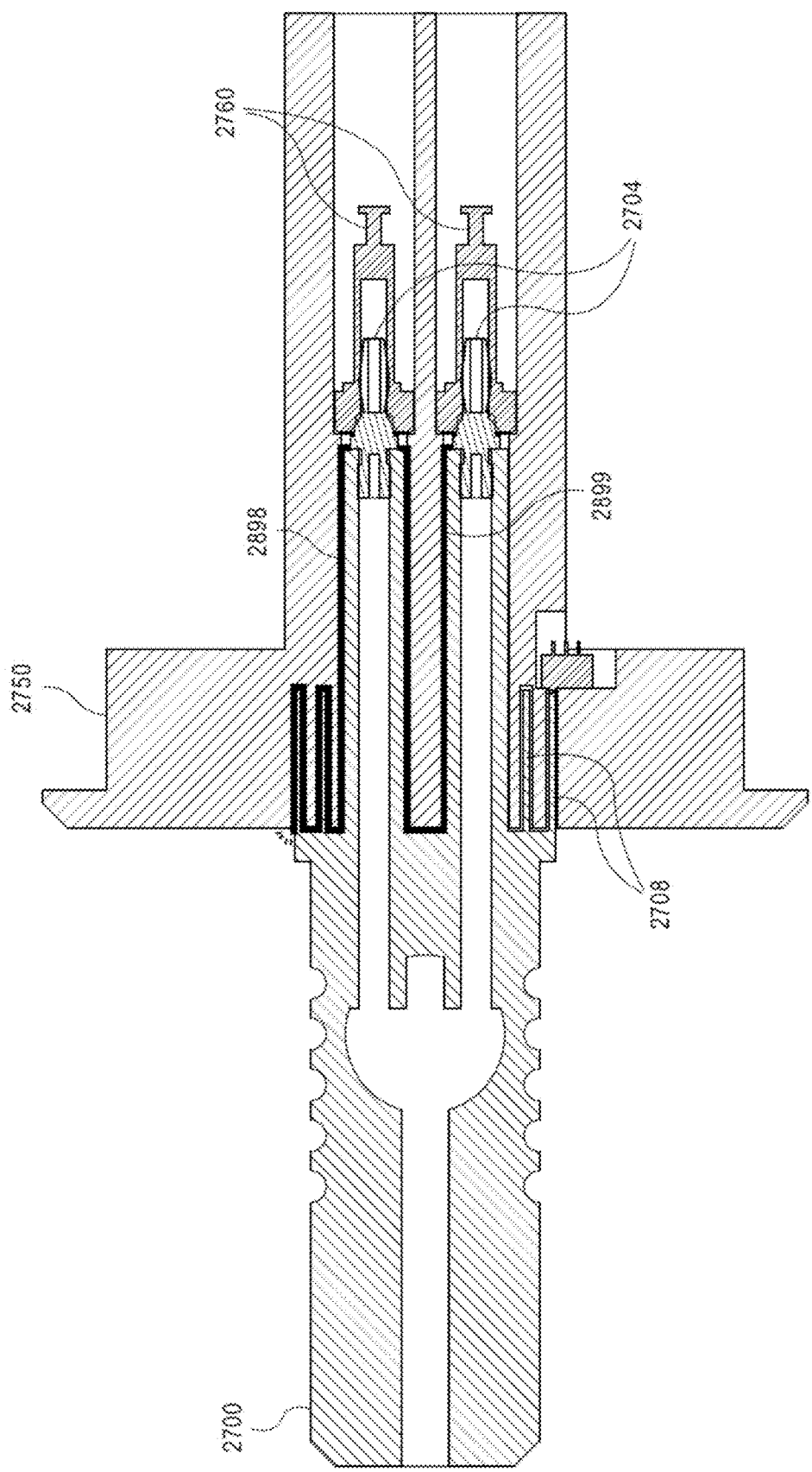
FIG. 15D shows a cross-section of a high-voltage connector and a housing cutaway portion with the connector engaged, and with a minimum clearance distance shown.

FIG. 15D illustrate examples of minimum clearance distances. Female terminals 2760 provide electrical power to male plug terminals 2704. Terminals 2760 are shielded from or are spaced a minimum clearance distance $d_{min\_user}$ 2898 apart from external portions of the housing which may be accessed by a hand or a finger of a user. The minimum clearance distance may be determined based at least in part on an expected voltage applied to terminals 2760 to ensure that the voltage is insufficient to cause a shock to a hand or finger of the user if placed the minimum clearance distance from the terminals 2760.

Minimum clearance distance 2898 to the user is measured by following surfaces out of the receptacle's holes, around dual skirts 2708, and to a user, as a hand of a user may be placed next to a visible seam between the connector 2700 when mated with the housing cutaway portion 2750 as shown. In some embodiments, the minimum clearance distance is at least 0.5, 0.85, 1.0, 1.27, 2.5, 3.2, 3.8, 4.4, 5.1, 6.4, 7.6, 10.2, 12.7, or more centimeters (i.e., 0.20, 0.33, 0.39, 0.5, 1, 1.25, 1.5, 1.75, 2, 2.5, 3, 4, 5, or more inches).

Figure 16:
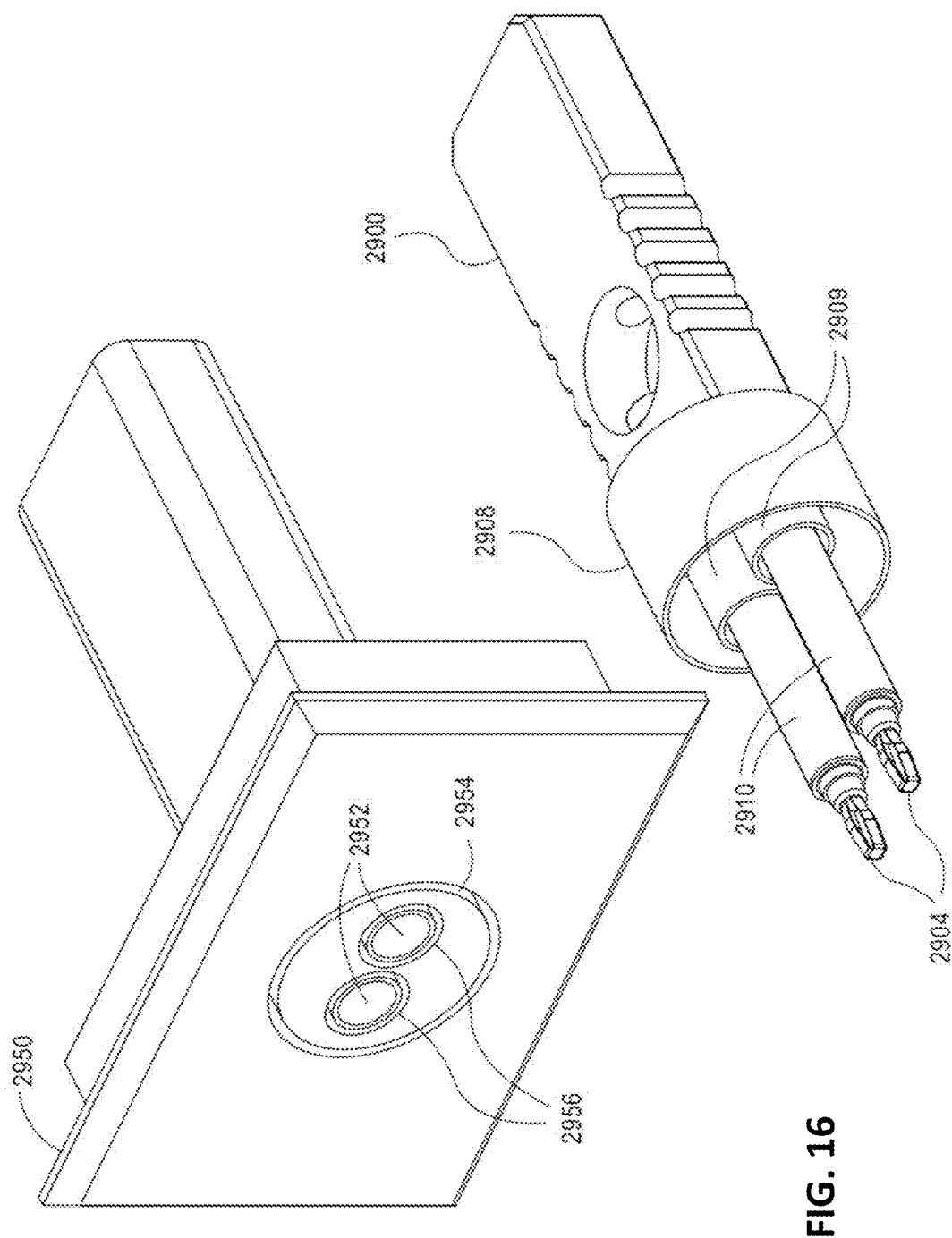
FIG. 16 is an illustration of a high-voltage connector configured to be mated with a pulse generator housing (shows as a partial cutaway portion).

FIG. 15D also shows an example of another minimum clearance distance 2899, which represents minimum clearance distance between terminals ($d_{min\_terminals}$) This distance $d_{min\_terminals}$ is described in more detail in references to FIG. 16. Either minimum clearance distance can be equal to or greater than 0.5, 0.85, 1.0, 1.27, 2.5, 3.2, 3.8, 4.4, 5.1, 6.4, 7.6, 10.2, 12.7, or more centimeters (i.e., 0.20, 0.33, 0.39, 0.5, 1, 1.25, 1.5, 1.75, 2, 2.5, 3, 4, 5, or more inches).

FIG. 16 is an illustration of connector 2900 configured to be mated with housing cutaway portion 2950. Connector 2900 may, for example, be used in a high-voltage, fast pulsing (e.g., sub-microsecond pulsing) system 100 to connect catheter 102 to housing 105. When mated, connector 2900 electrically connects catheter 102 with the electronic components internal to housing 105, such as a high-voltage, fast pulsing (e.g., sub-microsecond pulsing) pulse generator.

FIG. 16 illustrates connector 2900 and cutaway portion 2950 in an unmated position. As a comparison of exemplary embodiments, FIGS. 14A-14B illustrates insulative structures, such as the skirt 2708, configured to provide a minimum clearance distance between the user's fingers and/or hand and the conductive terminals. FIG. 16 illustrates additional novel features configured to provide a minimum clearance distance 2899 between the conductive terminals themselves, such as a minimum clearance distance $d_{min\_terminals}$, shown in FIG. 15D. The minimum clearance distance $d_{min\_terminals}$ provides protection against an arc between the conductive terminals and protects, for example, a patient.

The "minimum clearance distance between the terminals" ($d_{min\_terminals}$) as used herein includes a shortest distance that avoids an arc both in the air or along an insulating material surface path. In other words, $d_{min\_terminals}$ can include a distance that is the greater of the following two distances: 1) a shortest distance or path that prevents an arc between two conductive parts measured along any surface or combination of surfaces of an insulating material, and 2) a shortest path in air between two conductive parts that prevents an arc.

A "creepage distance" include a shortest distance that prevents arcs along the surface of the insulating material between two conductive parts, as defined by the International Electrotechnical Commission (IEC), or as otherwise known in the art. It can include the surface distance from one conductive part to another conductive part or an area accessible by a user.

"Air clearance" includes the shortest path that prevents arc in air between two conductive parts as defined by the IEC, or as otherwise known in the art. It can include the uninterrupted distance through the air or free space from one conductive part to another conductive part or an area accessible by a user.

Connector 2900 can include features similar to or identical to connector 2700 illustrated above in FIGS. 14A, 14B, 15A, 15B, and 15C. Connector 2900 includes standoff skirt 2908, which is similar to standoff skirt 2708 of connector 2700. In addition, connector 2900 includes additional standoff skirts 2909. As shown, standoff skirts 2909 each surround a portion of one of the spacers 2910. Standoff skirts 2909 maintain a desired separation between terminals 2904. Housing cutaway portion 2950 can include features similar to or identical to housing cutaway portion 2750 illustrated above in FIGS. 14A, 14B, 15A, 15B, 15C, and 15D.

In this embodiment, in addition to terminal receptacle holes 2952 and skirt receptacle hole 2954, housing cutaway portion 2950 also includes skirt receptacle holes 2956, which are configured to receive skirts 2909 of connector 2900 when connector 2900 is mated with housing cutaway portion 2950.

Figure 17A:
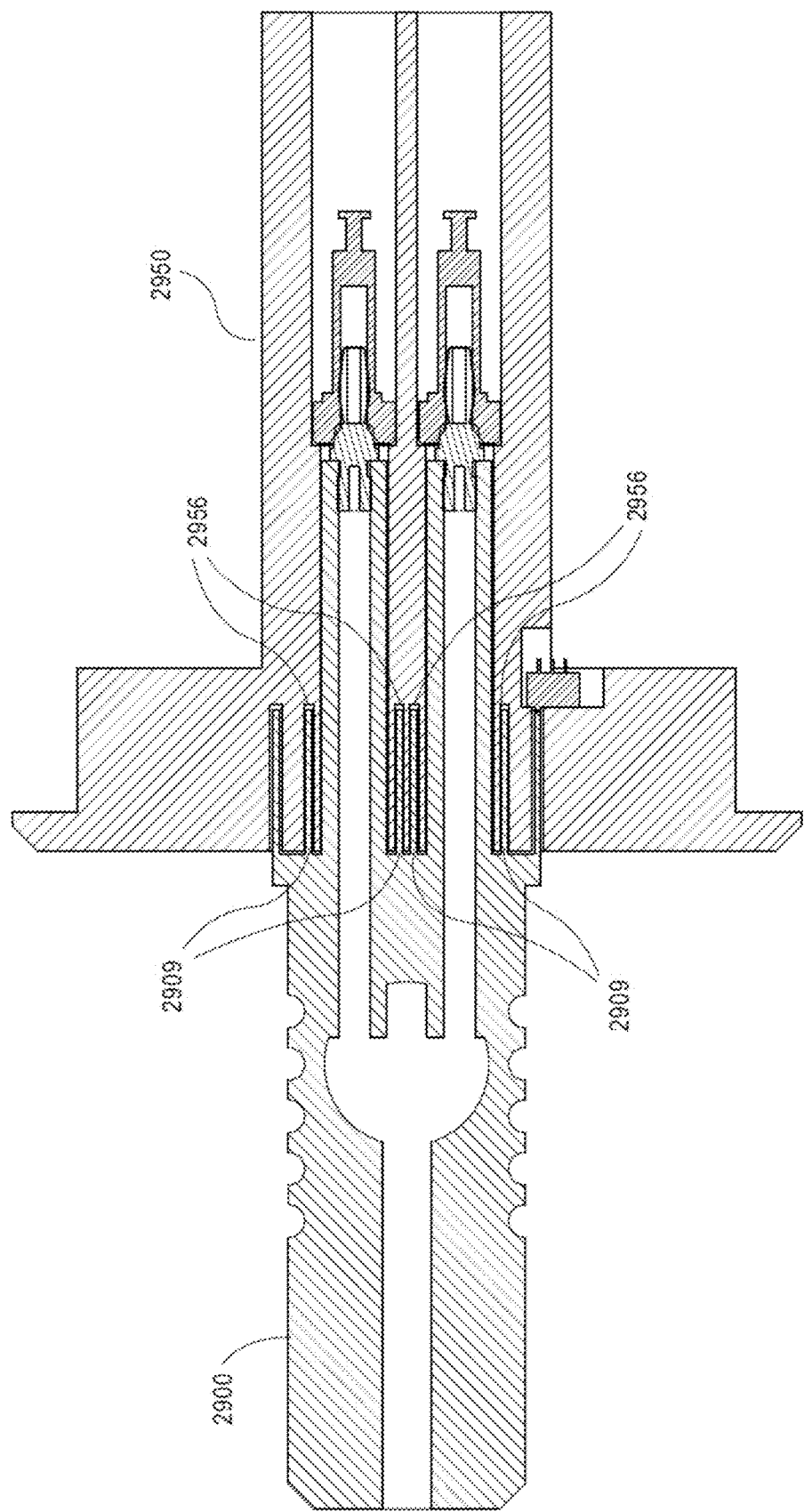
FIG. 17A shows a cross-section of a high-voltage connector and a portion of a housing (shown as a partial cutaway).
Figure 17B:
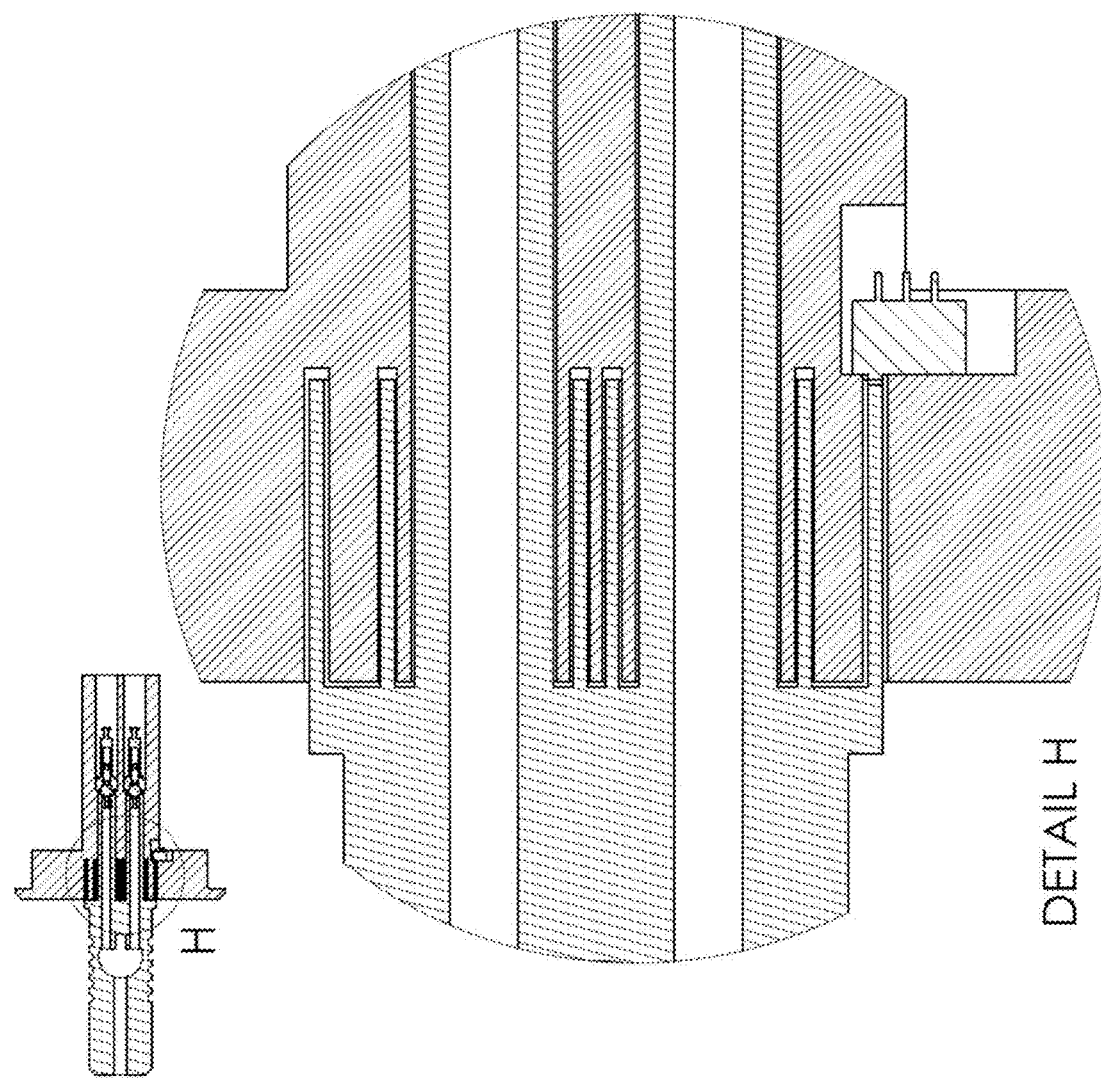
FIG. 17B is an illustration of a cross-sectional view of a high-voltage connector and a cutaway view of a portion of a pulse generator housing.

FIGS. 17A and 17B are illustrations of a cross-sectional view of connector 2900 and housing cutaway portion 2950. FIGS. 17A and 17B illustrate connector 2900 and cutaway portion 2950 in a mated position, where FIG. 17B illustrates in detail H an enlarged view of portions of connector 2900 and cutaway portion 2950.

In some embodiments, a high-voltage, fast pulsing (e.g., sub-microsecond pulsing) pulse generator may be connected with a cable to a therapeutic catheter, where the therapeutic catheter has terminals which are electrically connected to the cable by a connector/receptacle mating having characteristics similar or identical to one or more of connector 2700 and housing cutaway portion 2750 and connector 2900 and housing cutaway portion 2950.

Figure 18:
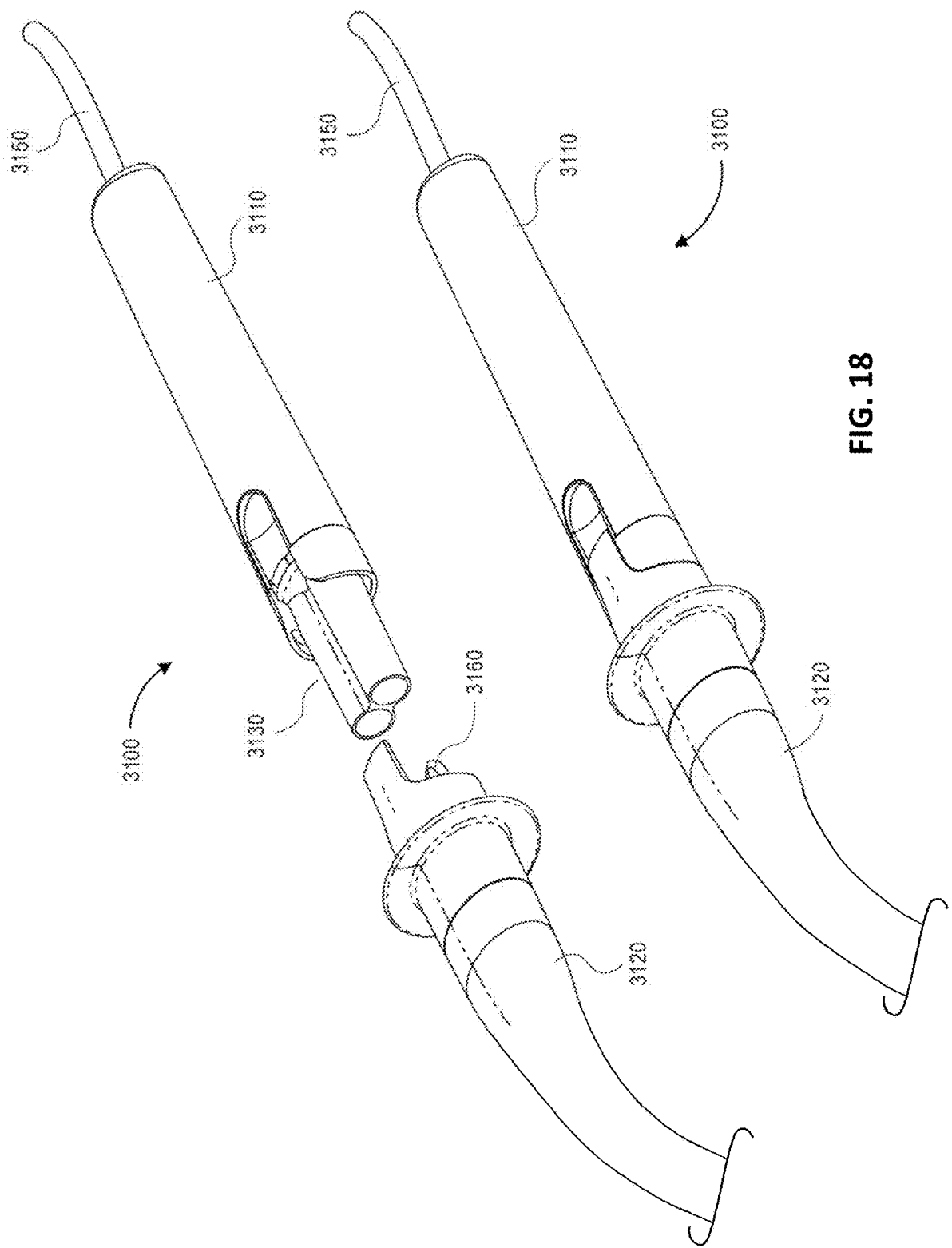
FIG. 18 illustrates an example of a high-voltage connector that may be used to couple a catheter to a pulse generator configured for the delivery of high voltage, fast pulses as described herein.

For example, FIG. 18 illustrates an intermediate connector 3100 which has therapeutic terminals (electrodes) which are connected to cable 3150 through conductors which run through catheter handle (or handle) 3110 and catheter 3120. The intermediate (handle) connector 3100 may be used in the high-voltage, fast pulsing (e.g., sub-microsecond pulsing) treatment systems discussed herein. For example, cable 3150 may be connected to a high-voltage, fast pulsing (e.g., sub-microsecond pulsing) pulse generator by another high-voltage connector (not shown) having features similar or identical to those of the connectors discussed elsewhere herein; the catheter may therefore be connected via a connector directly to the pulse generator or through an intermediate connector (e.g., connecting to a handle of the catheter, where one is included, as shown in FIG. 18.

As shown, the proximal end of the catheter 3120 may be removably connectable to a handle 3110. To connect catheter end 3120 to handle 3110, connection terminals 3160 may be inserted into skirt 3130. In some embodiments, the catheter end 3120 may be disposable, or may be discarded or disposed of after a single use.

Any of the apparatuses, including catheters and systems using them, may include one or more safety interlocking features to prevent the delivery of the high-voltage, very fast (e.g., sub-microsecond) pulsing until and unless the catheter is properly deployed and in contact with a tissue, e.g., target tissue. For example, the methods and apparatuses described herein may be configured to emit one or a pattern of test pulses at very low power (e.g., low voltage) including at high speed (e.g., sub-microsecond) to detect one or more properties of the electrical pathway including appropriate contact with a target tissue. In some variations, the apparatus may be configured to determine and detect the impedance at the one or more pairs of electrodes of the catheter to confirm that the contact with the tissue (and the electrical pathway from the pulse generator to the tissue) are correct. Thus, these apparatuses and methods of use may include measuring an impedance of the tissue with the electrodes (e.g., surface electrodes, needle electrodes, knife electrodes, etc.). In some examples, the electrodes can be used to measure the impedance of the target tissue to be treated as well as the surrounding tissue. For example, electrical energy can be applied to the target tissue at a known frequency. In a first example, the electrical energy can initially be a low-voltage pulsed energy until the electrodes are positioned appropriately against or within the target tissue. This proper positioning can be confirmed with the impedance measurement. Once the electrodes are positioned within or against the target tissue, the electrical energy can comprise high-voltage, fast pulsed energy, such as sub-microsecond pulses. However, it should be understood that in some application and embodiments any type of pulsed electrical energy can be applied to the target tissue (microsecond, nanosecond, picosecond, etc.).

During treatment of the tissue, treatment may continue if certain conditions are met, but may otherwise be terminated. For example, when a change in the impedance of the target tissue exceeds an impedance threshold, treatment may stop. Thus, the detection of contact and/or treatment may be ongoing during a treatment as well as before a treatment. For example, applying electrical energy to the tissue can change the impedance of the target tissue by breaking down the tissue itself. This change can be measured, and when the change in impedance exceeds an impedance threshold that indicates the tissue breakdown, the electrodes can be moved within the tissue or the treatment stopped. In another example, because the target tissue (e.g., tumor) may have different impedance from the surrounding tissue, a change in the impedance may occur because of the location of the catheter and electrodes relative to the target tissue. Therefore, this change can be measured, and when the change in impedance exceeds an impedance threshold that indicates that location of the electrodes is outside the target tissue, the electrodes can be moved or the treatment stopped. The movement of electrodes can occur either during each pulse or in between pulses, or during entire application of the electric energy. The impedance threshold may be, for example, between 0.1 kOhms and 100 kOhms, such as about 90 kOhms, about 80 kOhms, about 70 kOhms, about 60 kOhms, about 50 kOhms, about 40 kOhms, about 30 kOhms, about 25 kOhms, about 20 kOhms, about 15 kOhms, about 10 kOhms, about 5 kOhms, about 2.5 kOhms, about 1 kOhm, etc.).

The catheters and systems disclosed may be used in various methods and applications. For example, some of the methods comprise methods of delivering pulsed power to any of the apparatuses described herein, including in particular to a catheter. For example, a method may include: connecting a high-voltage connector to a first conductive layer and a second conductive layer of a catheter, the first conductive layer formed from a first plurality of filaments extending down at least a portion of a length of an elongate body of the catheter, the second conductive layer formed from a second plurality of filaments extending concentric to the first conductive layer. The method may further comprise applying a plurality of electrical pulses having an amplitude of 1 kV or more from the high-voltage connector through the first plurality of filaments and through the second plurality of filaments, wherein the first and second conductive layers are insulated by a flexible insulating material having a dielectric strength sufficient to withstand 2 kV or more. In some embodiments the electrical pulses may have an amplitude of between 1 kV and 15 kV, or between 1 kV and 9 kV, or any sub-range within the above ranges.

Further methods according to the present disclosure comprise methods of treating tissue. For example, the method of treating tissue may comprise: inserting a distal end of a catheter into a body, wherein the catheter comprises at least two electrodes at a distal end region; applying a plurality of electrical pulses having an amplitude of greater than 0.1 kV and a duration of less than 1000 nanoseconds to a proximal end of the catheter through a first plurality of filaments extending at least partially down the length of the catheter and through a second plurality of filaments extending at least partially down the length of the catheter; and delivering the applied plurality of electrical pulses to the body from a first electrode of the at least two electrodes in electrical communication with the first plurality of filaments and a second electrode of the at least two electrodes in electrical communication with the second plurality of filaments, wherein the first and the second plurality of filaments is configured and insulated to withstand 3 kV or more. The second plurality of filaments may extend concentrically over the first plurality of filaments.

As mentioned above, any of the apparatuses described herein may be implemented in robotic systems that may be used to position and/or control the electrodes during a treatment. For example, a system may include a robotic arm to which is coupled the catheter. Various motors and other movement devices may be incorporated to enable fine movements of an operating tip of the applicator in multiple directions. The robotic system and/or catheter may further include at least one image acquisition device (and preferably two for stereo vision, or more) which may be mounted in a fixed position or coupled (directly or indirectly) to a robotic arm or other controllable motion device.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

Certain embodiments may relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform or control performing of any of the steps, including but not limited to: displaying, communicating with the user, analyzing, modifying parameters (including timing, frequency, intensity, etc.), determining, alerting, or the like. In some exemplary embodiments hardware may be used in combination with software instructions to implement the present disclosure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "mounted", "connected", "attached" or "coupled" to another feature or element, it can be directly mounted, connected, attached or coupled to the other feature or element or intervening features or elements may be present. In contrast, when a feature or element is referred to as being "directly mounted", "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

The terms "comprises" and/or "comprising," when used in this specification (including the claims), specify the presence of stated features, steps, operations, elements, and/or components, but do not preclude the presence or addition of one or more other features, steps, operations, elements, components, and/or groups thereof. Unless the context requires otherwise, "comprise", and variations such as "comprises" and "comprising," means various components can be co-jointly employed in the methods and articles (e.g., compositions and apparatuses including device and methods). For example, the term "comprising" will be understood to imply the inclusion of any stated elements or steps but not the exclusion of any other elements or steps.

Any of the apparatuses and methods described herein may include all or a sub-set of the components and/or steps, and these components or steps may be either non-exclusive (e.g., may include additional components and/or steps) or in some variations may be exclusive, and therefore may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the apparatuses and methods as it is set forth in the claims.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating tissue, the method comprising:
   applying a plurality of electrical pulses having an amplitude of greater than 0.1 kV to a proximal end of a catheter inserted into a body of a subject through a first conductive layer formed from a first plurality of braided or woven filaments extending at least partially down a length of the catheter and through a second conductive layer extending coaxial to the first conductive layer; and
   delivering the plurality of electrical pulses to the body of the subject from a first electrode at a distal end region of the catheter in electrical communication with the first conductive layer and a second electrode at the distal end region of the catheter in electrical communication with the second conductive layer,
   wherein the first and second conductive layers are configured to prevent electromagnetic interference (EMI) arising from the first and second conductive layers at high voltages and rapid pulse rates.

2. The method of claim 1, further comprising connecting the catheter to a pulse generator using a high-voltage connector.

3. The method of claim 1, further comprising driving the distal end region of the catheter against the tissue so that the first and second electrodes contact the tissue.

4. The method of claim 1, further comprising inflating an inflatable balloon on a side of the distal end region of the catheter.

5. The method of claim 1, wherein each of the plurality of electrical pulses has a duration of 1000 ns or less.

6. The method of claim 1, wherein the plurality of electrical pulses has peak voltages of between about 1 kV/cm and 100 kV/cm.

7. The method of claim 1, wherein the first and second conductive layers are enclosed by a flexible insulating material having a dielectric strength sufficient to withstand 1 kV or more.

8. The method of claim 1, the method comprising a treatment of a cardiac tissue, esophageal tissue, lung tissue, bronchial passages, skin, or ablation of tumors.

9. The method of claim 1, wherein the method is to treat an epicardial, endocardial, and/or pericardial tissue, the method comprising positioning the catheter within or near a target region of a heart.

10. The method of claim 1, wherein at least one of the applying and delivering is performed by a robotic system.

11. The method of claim 1, further comprising checking an impedance between the first electrode and the second electrode prior to and/or while applying the plurality of electrical pulses and suspending the applying of the plurality of electrical pulses until the impedance exceeds an impedance threshold.

12. The method of claim 1, further comprising periodically or continuously checking an impedance between the first electrode and the second electrode during the applying of the plurality of electrical pulses and stopping or suspending the applying if the impedance falls below an impedance threshold or exceeds the impedance threshold.

13. The method of claim 1, the method comprising articulating at least some portion of the catheter by pulling and/or pushing one or more tendons or by using a bendable steering element in a lumen of the catheter.

14. The method of claim 1, wherein the method is for laparoscopic or endoscopic applications.

15. The method of claim 1, wherein at least one of the first electrode and the second electrode comprises one or more sets of electrodes and wherein the method comprises actuating the one or more sets of electrodes separately.

16. A method of delivering pulsed power to a catheter, the method comprising:
   allowing to connect or connecting a high-voltage connector to a first conductive layer and a second conductive layer of the catheter, the first conductive layer formed from a first one or more braided or woven filaments extending down at least a portion of a length of an elongate body of the catheter, the second conductive layer extending coaxial to the first conductive layer; and applying a plurality of electrical pulses having an amplitude of 1 kV or more from the high-voltage connector through the first and second conductive layers,
wherein the first and second conductive layers are insulated by a flexible insulating material and the first and second conductive layers are configured to prevent electromagnetic interference (EMI) arising from the first and second conductive layers at high voltages and rapid pulse rates.

17. The method of claim 16, the method comprising emitting one or a pattern of test pulses to detect at least one property of electrical pathway.

18. The method of claim 16, further comprising periodically or continuously checking an impedance between a first electrode at a distal end region of the catheter and a second electrode during the applying of the plurality of electrical pulses and stopping or suspending the applying if the impedance falls below an impedance threshold or exceeds the impedance threshold.

19. The method of claim 16, further comprising preventing energy from being applied through the high-voltage connector by one or more interlocks of the high-voltage connector until a sealing contact is ensured.

20. The method of claim 19, wherein ensuring the contact is performed by applying a low-power signal and determining a stability of a connection by detecting impedance or other electrical property.

21. The method of claim 16, further comprising connecting the catheter to a pulse generator through the high-voltage connector, wherein the pulse generator is configured to generate sub-microsecond pulses.

22. The method of claim 16, further comprising periodically or continuously checking an impedance between a first electrode and a second electrode of the catheter to determine whether a location of the first and second electrodes is outside of a target tissue.

23. The method of claim 16, further comprising delivering pulsed power from the catheter to a cardiac tissue.

* * * * *

UNITED STATES PATENT AND TRADEMARK OFFICE
CERTIFICATE OF CORRECTION

| | | |
|---|---|---|
| PATENT NO. | : 11,931,570 B2 | Page 1 of 1 |
| APPLICATION NO. | : 18/149665 | |
| DATED | : March 19, 2024 | |
| INVENTOR(S) | : David J. Danitz et al. | |

It is certified that error appears in the above-identified patent and that said Letters Patent is hereby corrected as shown below:

On the Title Page

Item (54); delete "TREATING TISSUE PULSED ENERGY USING HIGH-VOLTAGE CATHETERS" and insert --TREATING TISSUE WITH PULSED ENERGY USING HIGH-VOLTAGE CATHETERS--.

In the Specification

Column 1, Lines 1-2; delete "TREATING TISSUE PULSED ENERGY USING HIGH-VOLTAGE CATHETERS" and insert --TREATING TISSUE WITH PULSED ENERGY USING HIGH-VOLTAGE CATHETERS--.

Signed and Sealed this
Sixth Day of May, 2025

Coke Morgan Stewart
*Acting Director of the United States Patent and Trademark Office*